US012600712B2

(12) United States Patent
Beurier et al.

(10) Patent No.: US 12,600,712 B2
(45) Date of Patent: Apr. 14, 2026

(54) AMINO-PYRIMIDINE AMIDES

(71) Applicant: Hoffmann-La Roche Inc., Little Falls, NJ (US)

(72) Inventors: Angelica Beurier, Courtavon (FR); Michail Konstantinos Bogdos, Oberengstringen (CH); Luke Green, Basel (CH); Christian Kramer, Loerrach (DE); Dmitry Mazunin, Grenzach-Wyhlen (DE); Emmanuel Pinard, Lindsdorf (FR); Hasane Ratni, Habsheim (FR)

(73) Assignee: Hoffmann-La Roche Inc., Little Falls, NJ (US)

( * ) Notice: Subject to any disclaimer, the term of this patent is extended or adjusted under 35 U.S.C. 154(b) by 520 days.

(21) Appl. No.: 18/062,644

(22) Filed: Dec. 7, 2022

(65) Prior Publication Data

US 2023/0174516 A1 Jun. 8, 2023

Related U.S. Application Data

(63) Continuation of application No. PCT/EP2021/065111, filed on Jun. 7, 2021.

(30) Foreign Application Priority Data

Jun. 8, 2020 (EP) .................................... 20178651

(51) Int. Cl.
*C07D 403/06* (2006.01)
*C07D 491/107* (2006.01)

(52) U.S. Cl.
CPC ....... *C07D 403/06* (2013.01); *C07D 491/107* (2013.01)

(58) Field of Classification Search
CPC .......................... C07D 403/06; C07D 491/107
USPC ..................................................... 514/210.18
See application file for complete search history.

(56) References Cited

U.S. PATENT DOCUMENTS

| | | | |
|---|---|---|---|
| 2021/0363152 A1 | 11/2021 | Baccei et al. |
| 2023/0112172 A1 | 4/2023 | Brom et al. |
| 2023/0123268 A1 | 4/2023 | Beurier et al. |

FOREIGN PATENT DOCUMENTS

| | | | |
|---|---|---|---|
| JP | 2019-518799 A | 4/2019 |
| WO | 2018/212534 A1 | 11/2018 |
| WO | 2021/043260 A1 | 3/2021 |

OTHER PUBLICATIONS

Cancer [online], [retrieved on Jul. 6, 2007] Retrieved from the Internet, URL: http://www.nim.nih.gov/medlineplus/cancer.html (Year: 2007).*

Lala et al., Role of nitric oxide in tumor progression: Lessons from experimental tumors, Cancer and Metastasis Reviews (1998), 17, 91-106 (Year: 1998).*

Golub et al., Molecular Classification of Cancer: Class Discovery and Class Prediction by Gene Expression Monitoring, Science (1999), vol. 286, 531-537 (Year: 1999).*

International Preliminary Report on Patentability—PCT/EP2021/065111 issued Dec. 13, 2022, pp. 1-7.

International Search Report with Written Opinion—PCT/EP2021/065111 mailed Sep. 17, 2021, pp. 1-11.

"International Preliminary Report on Patentability—PCT/EP2021/065084" (Report Issuance Date: Dec. 13, 2022; Chapter I), pp. 1-7 (Dec. 22, 2022).

"International Preliminary Report on Patentability—PCT/EP2021/065106" (Report Issuance Date: Dec. 13, 2022; Chapter I), pp. 1-7 (Dec. 22, 2022).

"International Search Report—PCT/EP2021/065084" (w/Written Opinion), pp. 1-11 (Jul. 29, 2021).

"International Search Report—PCT/EP2021/065106" (w/Written Opinion), pp. 1-11 (Sep. 17, 2021).

* cited by examiner

*Primary Examiner* — Kristin A Vajda
(74) *Attorney, Agent, or Firm* — Sarah E. Tully

(57) ABSTRACT

The invention provides novel compounds having the general formula (I)

(I)

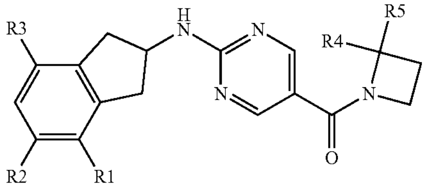

wherein $R^1$, $R^2$, $R^3$, $R^4$ and $R^5$ are as defined herein, compositions including the compounds and methods of using the compounds.

11 Claims, No Drawings

AMINO-PYRIMIDINE AMIDES

This application is a continuation of International Application No. PCT/EP2021/065111, filed Jun. 7, 2021, which claims the benefit of priority to EP Application No. 20178651.4, filed Jun. 8, 2020, the disclosures of each of which are incorporated herein by reference in their entireties.

The present invention relates to organic compounds useful for therapy or prophylaxis in a mammal, and in particular to autotaxin (ATX) inhibitors which are inhibitors of lysophosphatidic acid (LPA) production and thus modulators of LPA levels and associated signaling, for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

The present invention provides novel compounds of formula (I)

(I)

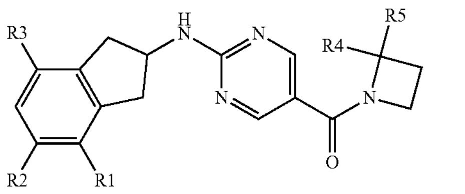

wherein $R^1$, $R^2$ and, $R^3$ are independently selected from the groups consisting of i) H, ii) $C_{1-6}$-alkyl, iii) $C_{2-6}$-alkynyl, iv) halogen, v) halo-$C_{1-6}$-alkyl vi) halo-$C_{1-6}$-alkoxy vii) cyano, viii) cyano-$C_{1-6}$-alkyl, wherein at least one of $R^1$ and $R^3$ are other than H;

$R^4$ and $R^5$ are independently selected from the groups consisting of i) H, ii) $C_{1-6}$-alkyl, or $R^4$ and $R^5$ together with the carbon atom to which they are attached form a heterocycloalkyl or a substituted $C_{3-8}$-cycloalkyl, wherein substituted $C_{3-8}$-cycloalkyl is substituted with $R^6$ and $R^7$;

$R^6$ and $R^7$ are independently selected from the groups consisting of halogen, hydroxy or alkyl.

or pharmaceutically acceptable salts.

Autotaxin (ATX) is a secreted enzyme also called ectonucleotide pyrophosphatase/phosphodiesterase 2 or lysophospholipase D that is important for converting lysophosphatidyl choline (LPC) to the bioactive signaling molecule lysophosphatidic acid (LPA). It has been shown that plasma LPA levels are well correlated with ATX activity and hence ATX is believed to be an important source of extracellular LPA. Early experiments with a prototype ATX inhibitor have shown that such a compound is able to inhibit the LPA synthesizing activity in mouse plasma. Work conducted in the 1970s and early 1980s has demonstrated that LPA can elicit a wide range of cellular responses; including smooth muscle cell contraction, platelet activation, cell proliferation, chemotaxis and others. LPA mediates its effects via signaling to several G protein coupled receptors (GPCRs); the first members were originally denoted Edg (endothelial cell differentiation gene) receptors or ventricular zone gene-1(vzg-1) but are now called LPA receptors. The prototypic group now consists of LPA1/Edg-2/VZG-1, LPA2/Edg-4, and LPA3/Edg-7. Recently, three additional LPA receptors LPA4/p2y9/GPR23, LPA5/GPR92 and LPA6/p2Y5 have been described that are more closely related to nucleotide-selective purinergic receptors than to the prototypic LPA1-3 receptors. The ATX-LPA signaling axis is involved in a large range of physiological and pathophysiological functions, including, for example, nervous system function, vascular development, cardiovascular physiology, reproduction, immune system function, chronic inflammation, tumor metastasis and progression, organ fibrosis as well as obesity and/or other metabolic diseases such as diabetes mellitus. Therefore, increased activity of ATX and/or increased levels of LPA, altered LPA receptor expression and altered responses to LPA may contribute to the initiation, progression and/or outcome of a number of different pathophysiological conditions related to the ATX/LPA axis.

In accordance with the invention, the compounds of formula (I) or their pharmaceutically acceptable salts and esters can be used for the treatment or prophylaxis of diseases, disorders or conditions that are associated with the activity of autotaxin and/or the biological activity of lysophosphatidic acid (LPA).

The compounds of formula (I) or their pharmaceutically acceptable salts and esters herein inhibit autotaxin activity and therefore inhibit LPA production and modulate LPA levels and associated signaling. Autotaxin inhibitors described herein are useful as agents for the treatment or prevention of diseases or conditions in which ATX activity and/or LPA signaling participates, is involved in the etiology or pathology of the disease, or is otherwise associated with at least one symptom of the disease. The ATX-LPA axis has been implicated for example in angiogenesis, chronic inflammation, autoimmune diseases, fibrotic diseases, cancer and tumor metastasis and progression, ocular conditions, metabolic conditions such as obesity and/or diabetes mellitus, conditions such as cholestatic or other forms of chronic pruritus as well as acute and chronic organ transplant rejection.

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of ATX and/or the biological activity of lysophosphatidic acid (LPA), particularly in the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection, and the use of the said compounds, salts or esters for the production of medicaments for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection. More particularly, the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of ocular conditions, furthermore particularly glaucoma.

As used herein, the terms "including," "containing," and "comprising" are used in their open, non-limiting sense.

The articles "a" and "an" as used in this disclosure may refer to one or more than one (e.g., to at least one) of the grammatical object of the article. By way of example, "an element" may mean one element or more than one element.

The term "$C_{1-6}$-alkoxy" denotes a group of the formula —O—R', wherein R' is a $C_{1-6}$-alkyl group. Examples of $C_{1-6}$-alkoxy group include methoxy, ethoxy, n-propoxy, isopropoxy, n-butoxy, isobutoxy and tert-butoxy. Particular examples are methoxy and isopropoxy.

The term "$C_{1-6}$-alkyl" denotes a monovalent linear or branched saturated hydrocarbon group of 1 to 6 carbon atoms. In some embodiments, if not otherwise described, alkyl comprises 1 to 6 carbon atoms ($C_{1-6}$-alkyl), or 1 to 4 carbon atoms ($C_{1-4}$-alkyl). Examples of $C_{1-6}$-alkyl include methyl, ethyl, propyl, isopropyl, n-butyl, iso-butyl, sec-butyl, tert-butyl and pentyl. Particular alkyl groups include methyl, isopropyl and tert-butyl. When an alkyl residue having a specific number of carbons is named, all geometric isomers having that number of carbons may be encompassed. Thus, for example, "butyl" can include n-butyl, sec-butyl, isobutyl and t-butyl, and "propyl" can include n-propyl and isopropyl.

The term "$C_{2-6}$-alkynyl" refers to an unsaturated unbranched or branched univalent hydrocarbon chain having at least one site of acetylenic unsaturation (that is, having at least one moiety of the formula C≡C). In some embodiments, unless otherwise specified, alkynyl comprises 2 to 6 carbon atoms ($C_{2-6}$-alkynyl), or 2 to 4 carbon atoms ($C_{2-4}$-alkynyl). Examples of alkynyl groups include, but are not limited to, ethynyl (or acetylenyl), prop-1-ynyl, prop-2-ynyl (or propargyl), but-1-ynyl, but-2-ynyl, and but-3-ynyl.

The term "cyano" denotes a —C≡N group.

The term "cyano-$C_{1-6}$-alkyl" denotes a $C_{1-6}$-alkyl group wherein one of the hydrogen atoms of the $C_{1-6}$-alkyl group is replaced by cyano group. Particular examples are cyanomethyl, cyanoethyl, cyanopropyl and cyanobutyl. Particular example is cyanopropyl.

The term "$C_{3-8}$-cycloalkyl" denotes monocyclic or polycyclic saturated or partially unsaturated, non-aromatic hydrocarbon. In some embodiments, unless otherwise described, cycloalkyl comprises 3 to 8 carbon atoms ($C_{3-8}$-cycloalkyl), 3 to 6 carbon atoms ($C_{3-6}$-cycloalkyl), or 3 to 5 carbon atoms ($C_{3-5}$-cycloalkyl). In some embodiments, cycloalkyl is a saturated monocyclic or polycyclic hydrocarbon. In other embodiments, cycloalkyl comprises one or more double bonds (e.g., cycloalkyl fused to an aryl or heteroaryl ring, or a non-aromatic monocyclic hydrocarbon comprising one or two double bonds). Polycyclic cycloalkyl groups may include spiro, fused, or bridged polycyclic moieties wherein each ring is a saturated or partially unsaturated, non-aromatic hydrocarbon. Examples of cycloalkyl groups include cyclopropyl, cyclobutyl, cyclopentyl, cyclohexyl, octahydropentalenyl, spiro[3.3]heptanyl, and the like. Bicyclic means a ring system consisting of two saturated carbocycles having two carbon atoms in common. Examples for monocyclic cycloalkyl are cyclopropyl, cyclobutanyl, cyclopentyl, cyclohexyl or cycloheptyl.

The term "halogen", "halide" and "halo" are used interchangeably herein and denote fluoro, chloro, bromo or iodo. Particular halogen is chloro.

The term "halo-$C_{1-6}$-alkoxy" denotes a $C_{1-6}$-alkoxy group wherein at least one of the hydrogen atoms of the $C_{1-6}$-alkoxy group has been replaced by the same or different halogen atoms. Particular examples are difluoromethoxy, trifluoromethoxy, difluoroethoxy and trifluoroethoxy. More particular example is trifluoromethoxy.

The term "halo-$C_{1-6}$-alkyl" denotes a $C_{1-6}$-alkyl group wherein at least one of the hydrogen atoms of the $C_{1-6}$-alkyl group has been replaced by the same or different halogen atoms. Particular examples are difluoromethyl, trifluoromethyl, difluoroethyl and trifluoroethyl. More particular example is trifluoromethyl.

The term "heterocycloalkyl", alone or in combination, denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two cycles having at least one ring atoms in common. The heterocycloalkyl group may be saturated or unsaturated, and unless otherwise specified, may comprise 5, 6, 7, 8 or 9 ring atoms, where ring atoms refer to the sum of carbon and heteroatoms in the one or more rings (e.g., be a 5-membered, 6-membered, 7-membered, 8-membered or 9-membered heterocycloalkyl). Heterocycloalkyl may include groups comprising 1 to 5 ring heteroatoms, 1 to 4 heteroatoms, 1 to 3 ring heteroatoms, 1 or 2 ring heteroatoms, or 1 ring heteroatom. In some embodiments, the heterocycloalkyl comprises one ring, two rings, three rings, or four rings, for example as a polycyclic fused system. In some embodiments, heterocycloalkyl comprising multiple rings includes spirocyclic systems in which one or more rings comprise one or more heteroatoms. Heterocycloalkyl examples are dihydrofuryl, imidazolinyl, dihydro-oxazolyl, tetrahydropyridinyl, or dihydropyranyl. Particular example is tetrahydropyranyl.

The term "hydroxy" denotes a —OH group.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention provides compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A particular embodiment of the present invention provides compounds according to formula (I) as described herein, wherein $R^1$, $R^2$ and, $R^3$ are independently selected from the groups consisting of
- i) H,
- ii) $C_{1-6}$-alkyl,
- iii) $C_{2-6}$-alkynyl,
- iv) halogen,
- v) halo-$C_{1-6}$-alkyl
- vi) halo-$C_{1-6}$-alkoxy,
- vii) cyano,
- viii) cyano-$C_{1-6}$-alkyl, wherein at least one of $R^1$ and $R^3$ are other than H;

$R^4$ and $R^5$ are independently selected from the groups consisting of
- i) H,
- ii) $C_{1-6}$-alkyl, or $R^4$ and $R^5$ together with the carbon atom to which they are attached form a heterocycloalkyl or a substituted $C_{3-8}$-cycloalkyl, wherein substituted cycloalkyl is substituted with $R^6$ and $R^7$;

$R^6$ and $R^7$ are independently selected from the groups consisting of halogen, hydroxy or alkyl.

or pharmaceutically acceptable salts.

A particular embodiment of the present invention provides compounds according to formula (I) as described herein, $R^1$, $R^2$ and, $R^3$ are independently selected from the groups consisting of
- i) H,
- ii) $C_{1-6}$-alkyl,
- iii) $C_{2-6}$-alkynyl,
- iv) halogen,
- v) halo-$C_{1-6}$-alkyl
- vi) halo-$C_{1-6}$-alkoxy,
- vii) cyano;

wherein at least one of $R^1$ and $R^3$ are other than H.

Another further particular embodiment of the present invention provides compounds according to formula (I) as described herein, wherein $R^4$ and $R^5$ are independently selected from the groups consisting of
- i) H,
- ii) $C_{1-6}$-alkyl, or $R^4$ and $R^5$ together with the carbon atom to which they are attached form a 4-member heterocycloalkyl with a single oxygen or a substituted $C_4$-cycloalkyl, wherein substituted cycloalkyl is substituted with $R^6$ and $R^7$;

Another further particular embodiment of the present invention provides compounds according to formula (I) as described herein, wherein $R^4$ and $R^5$ are independently selected from the groups consisting of
- i) H,
- ii) methyl, or $R^4$ and $R^5$ together with the carbon atom to which they are attached form an oxetane ring or a substituted $C_4$-cycloalkyl, wherein substituted cycloalkyl is substituted with $R^6$ and $R^7$;

Another further particular embodiment of the present invention provides compounds according to formula (I) as described herein, wherein $R^6$ and $R^7$ are both halogen; or $R^6$ is hydroxy and $R^7$ is alkyl.

Another further particular embodiment of the present invention provides compounds according to formula (I) as described herein, wherein $R^6$ and $R^7$ are both fluorine; or $R^6$ is hydroxy and $R^7$ is methyl.

In some embodiments, $R^4$ and $R^5$ together with the carbon to which they are attached form form a heterocycloalkyl ring. In certain embodiments, the heterocycloalkyl comprises one to three annular heteroatoms independently selected from the group consisting of O, N and S. In certain embodiments, $R^4$ and $R^5$ together with the carbon atom to which they are attached form a 4-member heterocycloalkyl with a single oxygen. In certain embodiments, $R^4$ and $R^5$ together with the carbon atom to which they are attached form an oxetane ring.

In some embodiments, $R^4$ and $R^5$ together with the carbon to which they are attached form a substituted $C_{3-8}$-cycloalkyl, wherein substituted cycloalkyl is substituted with $R^6$ and $R^7$. In certain embodiments, $R^4$ and $R^5$ together with the carbon atom to which they are attached form a substituted $C_4$-cycloalkyl, wherein substituted cycloalkyl is substituted with $R^6$ and $R^7$.

In some embodiments, $R^4$ and $R^5$ are both methyl.

In some embodiments, $R^6$ and $R^7$ are both halogen. In certain embodiments, $R^6$ and $R^7$ are both fluorine.

In some embodiments, $R^6$ is hydroxy and $R^7$ is methyl.

A particular embodiment of the present invention provides compounds according to formula I(a) as described herein, wherein $R^1$, $R^2$ and, $R^3$ are independently selected from the groups consisting of
- i) H,
- ii) $C_{1-6}$-alkyl,
- iii) $C_{2-6}$-alkynyl, iv) halogen,
v) halo-$C_{1-6}$-alkyl
vi) halo-$C_{1-6}$-alkoxy,
vii) cyano;
wherein at least one of $R^1$ and $R^3$ are other than H.
$R^4$ and $R^5$ are independently selected from the groups consisting of
i) H,
ii) $C_{1-6}$-alkyl,
or $R^4$ and $R^5$ together with the carbon atom to which they are attached form an oxetane ring or a substituted $C_4$-cycloalkyl, wherein substituted cycloalkyl is substituted with $R^6$ and $R^7$;
$R^6$ and $R^7$ are both halogen; or
$R^6$ is hydroxy and $R^7$ is alkyl.
or pharmaceutically acceptable salts.

A particular embodiment of the present invention provides compounds according to formula I(a) as described herein, wherein
$R^1$, $R^2$ and, $R^3$ are independently selected from the groups consisting of
i) H,
ii) $C_{1-6}$-alkyl,
iii) $C_{2-6}$-alkynyl,
iv) halogen,
v) halo-$C_{1-6}$-alkyl
vi) halo-$C_{1-6}$-alkoxy,
vii) cyano;
wherein at least one of $R^1$ and $R^3$ are other than H.
$R^4$ and $R^5$ are independently selected from the groups consisting of
i) H,
ii) methyl,
or $R^4$ and $R^5$ together with the carbon atom to which they are attached form an oxetane ring or a substituted $C_4$-cycloalkyl, wherein substituted cycloalkyl is substituted with $R^6$ and $R^7$;
$R^6$ and $R^7$ are both fluorine; or
$R^6$ is hydroxy and $R^7$ is methyl.
or pharmaceutically acceptable salts.

Particular examples of compounds of formula (I) as described herein are selected from
(2-((4-chloro-2,3-dihydro-1H-inden-2-yl)amino)pyrimidin-5-yl)(6-oxa-1-azaspiro[3.3]heptan-1-yl)methanone;
(2-((4,6-dichloro-2,3-dihydro-1H-inden-2-yl)amino)pyrimidin-5-yl)(6-oxa-1-azaspiro[3.3]heptan-1-yl)methanone;
(2-((6-chloro-4-methyl-2,3-dihydro-1H-inden-2-yl)amino)pyrimidin-5-yl)(6-oxa-1-azaspiro[3.3]heptan-1-yl)methanone;
(2-((4,5-dichloro-2,3-dihydro-1H-inden-2-yl)amino)pyrimidin-5-yl)(6-oxa-1-azaspiro[3.3]heptan-1-yl)methanone;
2-((5-(6-oxa-1-azaspiro[3.3]heptane-1-carbonyl)pyrimidin-2-yl)amino)-6-chloro-2,3-dihydro-1H-indene-4-carbonitrile;
(S)-2-((5-(6-oxa-1-azaspiro[3.3]heptane-1-carbonyl)pyrimidin-2-yl)amino)-6-chloro-2,3-dihydro-1H-indene-4-carbonitrile;
(2-((6-chloro-4-(difluoromethoxy)-2,3-dihydro-1H-inden-2-yl)amino)pyrimidin-5-yl)(6-oxa-1-azaspiro[3.3]heptan-1-yl)methanone;
(2-((5-chloro-4-methyl-2,3-dihydro-1H-inden-2-yl)amino)pyrimidin-5-yl)(6-oxa-1-azaspiro[3.3]heptan-1-yl)methanone;
(2-((6-chloro-4-(prop-1-yn-1-yl)-2,3-dihydro-1H-inden-2-yl)amino)pyrimidin-5-yl)(6-oxa-1-azaspiro[3.3]heptan-1-yl)methanone;
(2-((6-chloro-4-fluoro-2,3-dihydro-1H-inden-2-yl)amino)pyrimidin-5-yl)(6-oxa-1-azaspiro[3.3]heptan-1-yl)methanone;
(2-((5-chloro-4-fluoro-2,3-dihydro-1H-inden-2-yl)amino)pyrimidin-5-yl)(6-oxa-1-azaspiro[3.3]heptan-1-yl)methanone;
(S or R)-(2-((6-chloro-4-fluoro-2,3-dihydro-1H-inden-2-yl)amino)pyrimidin-5-yl)(6-oxa-1-azaspiro[3.3]heptan-1-yl)methanone;
(2-((6-chloro-4-(trifluoromethyl)-2,3-dihydro-1H-inden-2-yl)amino)pyrimidin-5-yl)(6-oxa-1-azaspiro[3.3]heptan-1-yl)methanone;
(S)-6-chloro-2-((5-(6,6-difluoro-1-azaspiro[3.3]heptane-1-carbonyl)pyrimidin-2-yl)amino)-2,3-dihydro-1H-indene-4-carbonitrile;
(S)-6-chloro-2-((5-(2,2-dimethylazetidine-1-carbonyl)pyrimidin-2-yl)amino)-2,3-dihydro-1H-indene-4-carbonitrile;
(cis)-6-chloro-2-(S)-((5-(6-hydroxy-6-methyl-1-azaspiro[3.3]heptane-1-carbonyl)pyrimidin-2-yl)amino)-2,3-dihydro-1H-indene-4-carbonitrile;
and pharmaceutically acceptable salts thereof.

Processes for the manufacture of compounds of formula (I) as described herein are an object of the invention.

The present compounds of formula I and their pharmaceutically acceptable salts can be prepared by methods known in the art, for example, by processes described below, which process comprises a) reacting a compound of formula

II

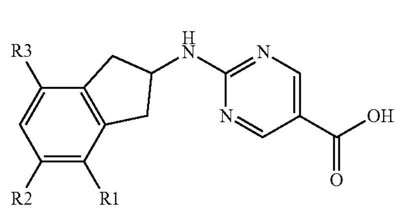

with a compound of formula

III

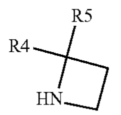

in the presence of an activating agent such as HATU (1-[Bis(dimethylamino)methylene]-1H-1,2,3-triazolo[4,5-b]pyridinium 3-oxid hexafluorophosphate) to a compound of formula

I

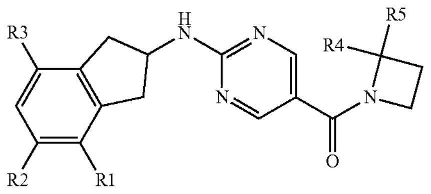

wherein the substituents are as defined above, or b) reacting a compound of formula

IV

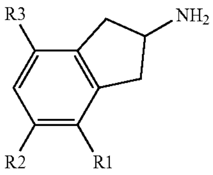

with a compound of formula

V

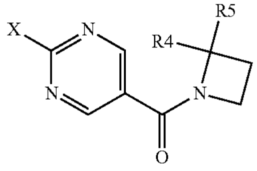

in the presence of a base like diisopropylethylamine to a compound of formula

I

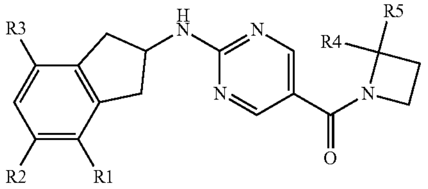

wherein X is halogen like Cl and the other substituents are as defined above, or if desired, converting the compounds obtained into pharmaceutically acceptable acid addition salts. The compounds of formula I may be prepared in accordance with process variant a) or b) and with the following schemes 1-2. The starting materials are commercially available or may be prepared in accordance with known methods.

Scheme 1

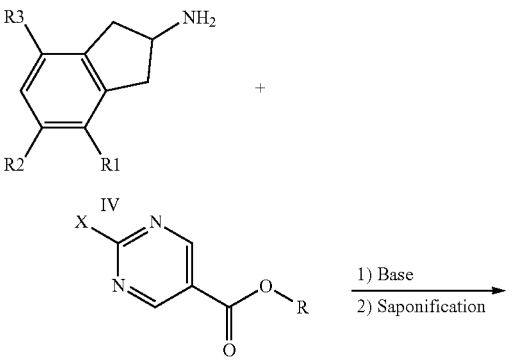

IV

VI

X: halogen

-continued

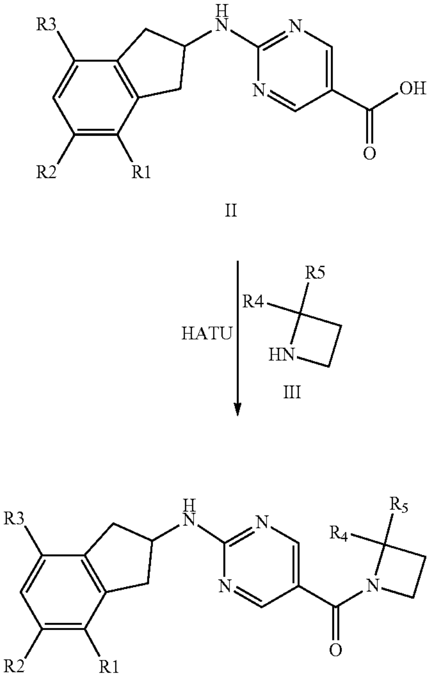

II

III

I

Compounds of general formula I can be prepared by reacting acid derivatives of formula II with an amine of formula III in the presence of an activating agent like HATU (1-[Bis (dimethylamino)methylene]-1H-1,2,3-triazolo[4,5-b]pyridinium 3-oxid hexafluorophosphate). The acid of formula II can be prepared by reaction of an amine of formula IV with an halogenated ester of formula VI in the presence of a base such as diisopropylethylamine, followed by saponification in the presence of a base like sodium or lithium hydroxide.

Scheme 2

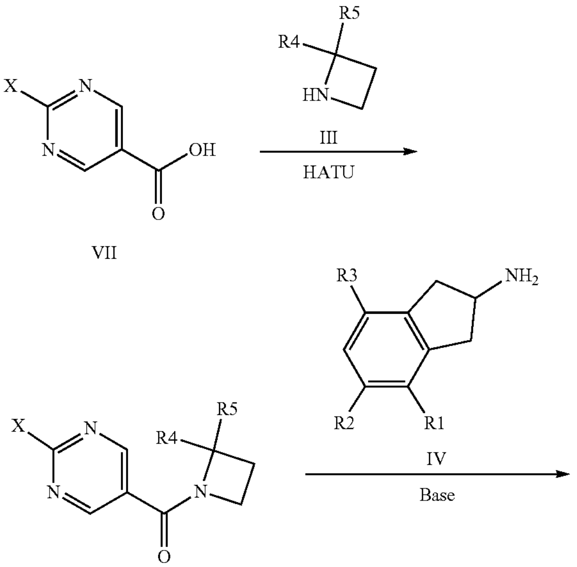

III

VII

IV

V

-continued

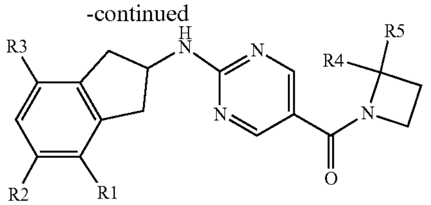

I

X: halogen

Alternatively, compounds of general formula I can be prepared by reacting halogenated derivatives of formula V with an amine of formula IV in the presence of a base like diisopropylethylamine. The halogenated derivative of formula V can be prepared by reaction of an amine of formula III with an acid of formula VII in the presence of an activating agent like 1-propanephosphonic anhydride.

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

An object of the invention is the use of a compound according to formula (I) as described herein for the treatment or prophylaxis of renal conditions, liver conditions, inflammatory conditions, conditions of the nervous system, conditions of the respiratory system, vascular and cardiovascular conditions, fibrotic diseases, cancer, ocular conditions, metabolic conditions, cholestatic and other forms of chronic pruritus and acute and chronic organ transplant rejection.

Renal conditions include, but are not limited to, acute kidney injury and chronic renal disease with and without proteinuria including end-stage renal disease (ESRD). In more detail, this includes decreased creatinine clearance and decreased glomerular filtration rate, micro-albuminuria, albuminuria and proteinuria, glomerulosclerosis with expansion of reticulated mesangial matrix with or without significant hypercellularity (particularly diabetic nephropathy and amyloidosis), focal thrombosis of glomerular capillaries (particularly thrombotic microangiopathies), global fibrinoid necrosis, ischemic lesions, malignant nephrosclerosis (such as ischemic retraction, reduced renal blood flow and renal arteriopathy), swelling and proliferation of intracapillary (endothelial and mesangial) and/or extracapillary cells (crescents) like in glomerular nephritis entities, focal segmental glomerular sclerosis, IgA nephropathy, vasculitides/systemic diseases as well as acute and chronic kidney transplant rejection.

Liver conditions include, but are not limited to, liver cirrhosis, hepatic congestion, cholestatic liver disease including pruritus, nonalcoholic steatohepatitis and acute and chronic liver transplant rejection.

Inflammatory conditions include, but are not limited to, arthritis, osteoarthritis, multiple sclerosis, systemic lupus erythematodes, inflammatory bowel disease, abnormal evacuation disorder and the like as well as inflammatory airways diseases such as idiopathic pulmonary fibrosis (IPF), chronic obstructive pulmonary disease (COPD) or chronic asthma bronchiale.

Further conditions of the respiratory system include, but are not limited to, other diffuse parenchymal lung diseases of different etiologies including iatrogenic drug-induced fibrosis, occupational and/or environmental induced fibrosis, systemic diseases and vasculitides, granulomatous diseases (sarcoidosis, hypersensitivity pneumonia), collagen vascular disease, alveolar proteinosis, Langerhans cell granulomatosis, lymphangioleiomyomatosis, inherited diseases (Hermansky-Pudlak Syndrome, tuberous sclerosis, neurofibromatosis, metabolic storage disorders, familial interstitial lung disease), radiation induced fibrosis, silicosis, asbestos induced pulmonary fibrosis or acute respiratory distress syndrome (ARDS).

Conditions of the nervous system include, but are not limited to, neuropathic pain, schizophrenia, neuro-inflammation (e.g. astrogliosis), peripheral and/or autonomic (diabetic) neuropathies and the like.

Vascular conditions include, but are not limited to, atherosclerosis, thrombotic vascular disease as well as thrombotic microangiopathies, proliferative arteriopathy (such as swollen myointimal cells surrounded by mucinous extracellular matrix and nodular thickening), atherosclerosis, decreased vascular compliance (such as stiffness, reduced ventricular compliance and reduced vascular compliance), endothelial dysfunction and the like.

Cardiovascular conditions include, but are not limited to, acute coronary syndrome, coronary heart disease, myocardial infarction, arterial and pulmonary hypertension, cardiac arrhythmia such as atrial fibrillation, stroke and other vascular damage.

Fibrotic diseases include, but are not limited to myocardial and vascular fibrosis, renal fibrosis, liver fibrosis, pulmonary fibrosis, skin fibrosis, scleroderma and encapsulating peritonitis.

Cancer and cancer metastasis include, but are not limited to, breast cancer, ovarian cancer, lung cancer, prostate cancer, mesothelioma, glioma, hepatic carcinoma, gastrointestinal cancers and progression and metastatic aggressiveness thereof.

Ocular conditions include, but are not limited to, proliferative and non-proliferative (diabetic) retinopathy, dry and wet age-related macular degeneration (AMD), macular edema, central arterial/venous occlusion, traumatic injury, glaucoma and the like. Particularly, the ocular condition is glaucoma.

Metabolic conditions include, but are not limited to, obesity and diabetes.

The present invention also relates to the use of a compound according to formula (I) as described herein for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the treatment or prophylaxis of renal conditions, liver conditions and fibrotic diseases.

A particular embodiment of the present invention is a compound according to formula (I) as described herein for the treatment or prophylaxis of renal conditions, liver conditions, inflammatory conditions, conditions of the nervous system, fibrotic diseases and acute and chronic organ transplant rejection.

A particular embodiment of the present invention is a compound according to formula (I) as described herein for the treatment or prophylaxis of renal conditions, liver conditions and fibrotic diseases.

The present invention also relates to the use of a compound according to formula (I) as described herein for the preparation of a medicament for the treatment or prophylaxis of renal conditions, liver conditions, inflammatory conditions, conditions of the nervous system, fibrotic diseases and acute and chronic organ transplant rejection.

The present invention also relates to the use of a compound according to formula (I) as described herein for the preparation of a medicament for the treatment or prophylaxis of renal conditions, liver conditions and fibrotic diseases.

Also an object of the invention is a method for the treatment or prophylaxis of renal conditions, liver conditions, inflammatory conditions, conditions of the nervous system, fibrotic diseases and acute and chronic organ transplant rejection, which method comprises administering an effective amount of a compound according to formula (I) as described herein.

Also an object of the invention is a method for the treatment or prophylaxis of renal conditions, liver conditions and fibrotic diseases, which method comprises administering an effective amount of a compound according to formula (I) as described herein.

Also an embodiment of the present invention provides compounds of formula (I) as described herein, when manufactured according to any one of the described processes.

Assay Procedures

Production of Human Full Length ATX, with and without His Tag

Autotaxin (ATX-ENPP2) cloning: cDNA was prepared from commercial human hematopoietic cells total RNA and used as template in overlapping PCR to generate a full length human ENPP2 ORF with or without a 3'-6×His tag. These full-length inserts were cloned into the pcDNA3.1V5-His TOPO (Invitrogen) vector. The DNA sequences of several single clones were verified. The DNA from a correct full-length clone was used to transfect Hek293 cells for verification of protein expression. The sequence of the encoded ENPP2 conforms to Swissprot entry Q13822, with or without the additional C-terminal 6×His tag.

ATX Fermentation: Recombinant protein was produced by large-scale transient transfection in 20 L controlled stirred tank bioreactors (Sartorius). During cell growth and transfection, temperature, stirrer speed, pH and dissolved oxygen concentration were maintained at 37° C., 120 rpm, 7.1 and 30% DO, respectively. FreeStyle 293-F cells (Invitrogen) were cultivated in suspension in FreeStyle 293 medium (Invitrogen) and transfected at ca. 1-1.5×10E6 cells/mL with above plasmid DNAs using X-tremeGENE Ro-1539 (commercial product, Roche Diagnostics) as complexing agent. Cells were fed a concentrated nutrient solution (J Immunol Methods 194 (1996), 19, 1-199 (page 193)) and induced by sodium butyrate (2 mM) at 72 h post-transfection and harvested at 96 h post-transfection. Expression was analyzed by Western Blot, enzymatic assay and/or analytical IMAC chromatography. After cooling the cell suspension to 4° C. in a flow-through heat exchanger, cell separation and sterile filtration of supernatant was performed by filtration through Zeta Plus 60M02 E16 (Cuno) and Sartopore 2 XLG (Sartorius) filter units. The supernatant was stored at 4° C. prior to purification.

ATX Purification: 20 liter of culture supernatant were conditioned for ultrafiltration by adding Brij 35 to a final concentration of 0.02% and by adjusting the pH to 7.0 using 1 M HCl. Then the supernatant was first microfiltred through a 0.2 pm Ultran-Pilot Open Channel PES filter (Whatman) and afterwards concentrated to 1 liter through an Ultran-Pilot Screen Channel PES filter with 30 kDa MWCO (Whatman). Prior to IMAC chromatography, NiSO4 was added to a final concentration of 1 mM. The cleared supernatant was then applied to a HisTrap column (GE Healthcare) previously equilibrated in 50 mM Na2HPO4 pH 7.0, 0.5 M NaCl, 10% glycerol, 0.3% CHAPS, 0.02% NaN3. The column was washed stepwise with the same buffer containing 20 mM, 40 mM and 50 mM imidazole, respectively. The protein was subsequently eluted using a linear gradient to 0.5 M imidazole in 15 column volumes. ATX containing fractions were pooled and concentrated using an Amicon cell equipped with a 30 kDa PES filter membrane. The protein was further purified by size exclusion chromatography on Superdex S-200 prep grade (XK 26/100) (GE Healthcare) in 20 mM BICINE pH 8.5, 0.15 M NaCl, 10% glycerol, 0.3% CHAPS, 0.02% NaN3. Final yield of protein after purification was 5-10 mg ATX per liter of culture supernatant. The protein was stored at −80° C.

Human ATX Enzyme Inhibition Assay

To identify inhibitors of the human Autotaxin (ATX) enzyme an in-vitro biochemical profiling assay has been developed using lysophosphatidylcholine (LPC) as substrate and recombinant enzyme. ATX activity is assayed via a coupled enzyme format where choline produced from LPC hydrolysis is converted to hydrogen peroxide by choline oxidase (CO). Hydrogen peroxide is in turn used as a co-substrate by horseradish peroxidase (HRP) to oxidise Amplex Red® and generate the red-fluorescent product, Resorufin.

Materials/Reagents 500 mM Tris-HCl pH 8.0; 1M NaCl; 250 mM $CaCl_2$; 250 mM KCl; 250 mM $MgCl_2$; 10% Triton X-100 in $H_2O$.

Assay Buffer 50 mM Tris-HCl (pH 8.0); 120 mM NaCl; 20 mM $CaCl_2$); 5 mM KCl; 1 mM $MgCl_2$; 0.01% Triton X-100, sterile-filtered and stored at 4° C.

Reagent Dilution Buffer 50 mM Tris-HCl (pH 8.0); 150 mM NaCl human Autotaxin (hATX): 0.97 mg/ml (9.718 μM) Molecular weight 99817. Working solution of 1.5 μM used in this assay.

100 mM 18:1 LPC dissolved in reagent dilution-buffer.

500 U/ml Choline Oxidase in reagent dilution buffer.

2540 U/ml Horseradish Peroxidase, in reagent dilution buffer (10.95 mg/ml).

20 mM Amplex Red (10-Acetyl-3,7-dihydroxy-phenoxazin) in DMSO.

Reaction Plate

Black, 384-well plate, black with clear bottom, non-treated surface.

Test compounds are received pre-diluted in DMSO as an 11-point concentration-response (0.5 mM highest concentration; 1 in 3.162 dilution). Test compounds are pre-diluted 1:1 (10 μL compound+10 μL assay buffer) in a 96-well conical bottomed plate prior to use.

Procedure

ATX is diluted to 2.2 nM in assay buffer. Choline oxidase and horseradish peroxidase are diluted to 7.3 U/ml and 14.7 U/ml, respectively. 18:1 LPC and Amplex Red® are diluted to 110 μM and 183.3 μM, respectively (solution protected from light). 2.2 μL of compound pre-dilution or 50% DMSO is added to the reaction plate followed by 25 μL of ATX or assay buffer (negative control). Assay plate is mixed and incubated at room temperature for 10 mins. 15 μL of choline oxidase/horseradish peroxidase is then added. To initiate the reaction 15 μL of LPC 18:1/Amplex Red is added. Assay plate is mixed and incubated at room temperature in the dark. Fluorescence is measured at 5 mins (for background subtraction) and 90 mins.

Final Assay Concentrations:

hATX: 1 nM

18:1 LPC: 30 μM

Choline Oxidase: 2 U/ml

Horse Radish Peroxidase: 4 U/ml

Amplex Red®: 50 μM

DMSO: 2%

Fluorescence at 5-minutes is subtracted from the 90-minute end point data and normalized with respect to the positive control. $IC_{50}$ values are calculated.

Results in the enzymatic ATX inhibition assay are provided for compounds of formula (I).

TABLE 1

| Example | ATX IC50 [μM] |
|---|---|
| 1 | 0.013 |
| 2 | 0.062 |
| 3 | 0.1284 |
| 4 | 0.0208 |
| 5 | 0.2238 |
| 6 | 0.1011 |
| 7 | 0.0237 |
| 8 | 0.1113 |
| 9 | 0.1233 |
| 10 | 0.1838 |
| 11 | 0.0074 |
| 12 | 0.0065 |
| 13 | 0.003 |
| 14 | 0.0055 |
| 15 | 0.2818 |
| 16 | 0.0451 |

Compounds of formula (I) and their pharmaceutically acceptable salts or esters thereof as described herein have $IC_{50}$ values between 0.0055 μM and 0.2818 μM. These results have been obtained by using the enzymatic assay described above.

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

All examples and intermediates were prepared under nitrogen atmosphere if not specified otherwise.

INTERMEDIATES A

Intermediate A1: 4,6-dichloro-2,3-dihydro-1H-inden-2-aminium 2,2,2-trifluoroacetate

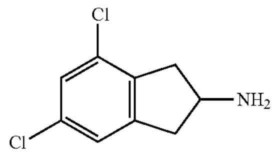

TFA salt

Step 1: 4-(4,4,5,5-tetramethyl-1,3,2-dioxaborolan-2-yl)-2,3-dihydro-1H-inden-2-yl)carbamate

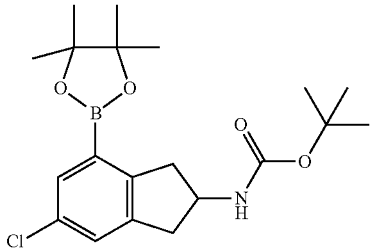

4,4,4',4',5,5,5',5'-octamethyl-2,2'-bi(1,3,2-dioxaborolane) (2.42 g, 9.34 mmol), (1,5-cyclooctadiene)(methoxy) iridium (I) dimer (309 mg, 467 μmol), tert-butyl (5-chloro-2,3-dihydro-1H-inden-2-yl)carbamate (2.50 g, 9.34 mmol, CAS: 1934835-81-0) and 3,4,7,8-tetramethyl-1,10-phenanthroline (221 mg, 934 μmol) were combined in a microwave vial (dried using high vacuum and flushed with Argon) and were suspended in dry THF (10 ml). On mixing these reagents, the suspension turned dark green. Argon was bubbled through the suspension for 10 min. The reaction mixture was heated to 80° C. and stirred for 15 h (turned dark violet). The reaction mixture was filtered through sintered glass and concentrated in vacuo. The crude material was purified by flash chromatography over silica gel using a gradient ethylacetate/heptane 0-30% to provide the title compound as an off-white solid (2.30 g, 63% yield). MS (ESI): m/z=294.2 $[M\text{-}Boc+H]^+$ Step 2: tert-butyl (4,6-dichloro-2,3-dihydro-1H-inden-2-yl)carbamate

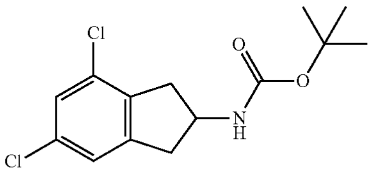

4-(4,4,5,5-tetramethyl-1,3,2-dioxaborolan-2-yl)-2,3-dihydro-1H-inden-2-yl)carbamate (100 mg, 254 μmol) was dissolved in EtOH (2.54 ml) and added to a solution of copper (II) chloride (104 mg, 775 μmol) in distilled water (2.54 ml). The reaction was heated to 90° C. for 6 hours, poured into water and extracted with EtOAc. The layers were separated and the aqueous layer was extracted twice more with EtOAc. The combined organic layers were washed with brine, dried over anhydrous sodium sulfate and evaporated to dryness. The crude product was purified by flash chromatography over silica gel using a gradient ethylacetate/heptane 0-50% to provide the title compound as a brown solid (20 mg, 26% yield). MS (ESI): m/z=246.1 [M-tBu]

Step 3: 4,6-dichloro-2,3-dihydro-1H-inden-2-aminium 2,2,2-trifluoroacetate

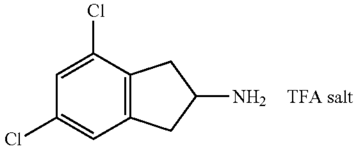

tert-butyl (4,6-dichloro-2,3-dihydro-1H-inden-2-yl)carbamate (17 mg, 56.3 μmol, Eq: 1) was dissolved in TFA (811 μl) and stirred at rt for 1 hour. Evaporation of the solvent provide the title compound (13 mg, 41.1 μmol, 73.1% yield) as a colourless oil. MS (ESI): m/z=202.1 M-TFA Intermediate A2: 6-chloro-4-methyl-2,3-dihydro-1H-inden-2-aminium chloride

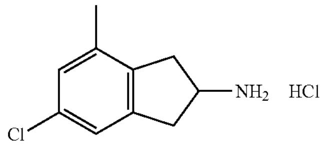

Step 1: Tert-butyl (6-chloro-4-hydroxy-2,3-dihydro-1H-inden-2-yl)carbamate

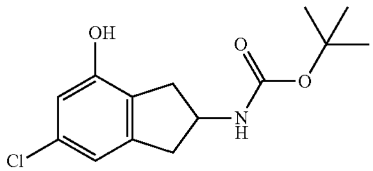 [SMILES: CC(C)(C)OC(=O)NC1Cc2cc(Cl)cc(O)c2C1]

4-(4,4,5,5-tetramethyl-1,3,2-dioxaborolan-2-yl)-2,3-dihydro-1H-inden-2-yl)carbamate (intermediate A1, step 1) (850 mg, 1.84 mmol) was dissolved in THF (5.56 ml) and water (556 μl) and sodium berborate monohydrate (549 mg, 5.51 mmol) was added. The reaction was stirred at rt for 18 hours. The solvent was evaporated and the residue was taken up in water and extracted with EtOAc. The layers were separated and the aqueous layer was extracted twice more with EtOAc. The combined organic layers were washed with brine, dried over anhydrous sodium sulfate and evaporated to dryness. The crude product was subjected to flash chromatography over silica gel using a gradient ehylacetate/heptane 0-50% to provide the title compound as a off-white solid (220 mg, 42% yield). MS (ESI): m/z=282.2 $[M-H]^+$ Step 2: 2-((tert-butoxycarbonyl)amino)-6-chloro-2,3-dihydro-1H-inden-4-yl trifluoromethanesulfonate

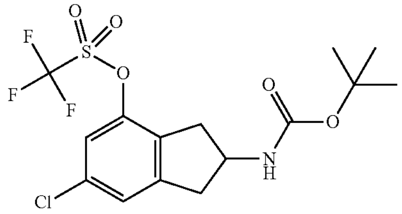 [SMILES: CC(C)(C)OC(=O)NC1Cc2cc(Cl)cc(OS(=O)(=O)C(F)(F)F)c2C1]

Tert-butyl (6-chloro-4-hydroxy-2,3-dihydro-1H-inden-2-yl)carbamate (50 mg, 176 μmol) was dissolved in dry DCM (705 μl) and triethylamine (19.6 mg, 27 μl, 194 μmol) was added. To this stirred solution, 1,1,1-trifluoro-N-phenyl-N-((trifluoromethyl)sulfonyl)methanesulfonamide (69.2 mg, 194 μmol) was added. The reaction was stirred at rt for 3 hours, poured into water and extracted with EtOAc. The layers were separated and the aqueous layer was extracted twice with EtOAc. The combined organic layers were washed with brine, dried over anhydrous sodium sulfate and evaporated to dryness. The crude product was subjected to flash chromatography over silica gel using a gradient ehylacetate/heptane 0-50% to provide the title compound as a white solid (42 mg, 57% yield). MS (ESI): m/z=414.1 [M–H]+

Step 3: Tert-butyl (6-chloro-4-methyl-2,3-dihydro-1H-inden-2-yl)carbamate

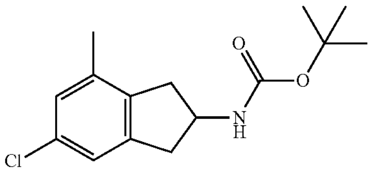 [SMILES: Cc1cc(Cl)cc2c1CC(NC(=O)OC(C)(C)C)C2]

Potassium trifluoro(methyl)borate (17.6 mg, 144 μmol) was suspended in THF (1.31 ml). Cesium carbonate (141 mg, 433 μmol), Bis(diphenylphosphino)ferrocene] dichloropalladium(II) dichloromethane complex (11.8 mg, 14.4 μmol) and 2-((tert-butoxycarbonyl)amino)-6-chloro-2,3-dihydro-1H-inden-4-yl trifluoromethanesulfonate (60 mg, 144 μmol) were added, followed by water (131 μl). Argon was bubbled through the reaction for 5 minutes and then the reaction was heated to 80° C. for 22 hours. The reaction was poured into water and extracted with EtOAc. The layers were separated and the aqueous layer was extracted twice more with EtOAc. The combined organic layers were washed with brine, dried over anhydrous sodium sulfate and evaporated to dryness. The crude product was subjected to flash chromatography over silica gel using a gradient ehylacetate/heptane 0-50% to provide the title compound as a colorless oil (24 mg, 53% yield). MS (ESI): m/z=226.1 [M-tBu]+

Step 4: 6-chloro-4-methyl-2,3-dihydro-1H-inden-2-aminium chloride

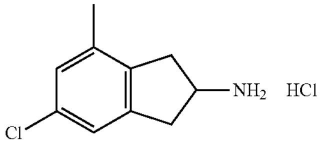

Tert-butyl (6-chloro-4-methyl-2,3-dihydro-1H-inden-2-yl)carbamate (25 mg, 79.8 μmol) was dissolved in HCl 4 M in dioxane (1.01 ml) and stirred at rt for 1 hour. Evaporation of the solvent afforded the title compound (17 mg, 97.6% yield) as a white solid. MS (ESI): m/z=182.1 [M+H]+

Intermediate A3: 4,5-dichloro-2,3-dihydro-1H-inden-2-aminium chloride

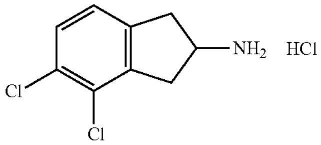 [SMILES: NC1Cc2ccc(Cl)c(Cl)c2C1 ; Cl]

Step 1: tert-butyl (5-amino-4-chloro-2,3-dihydro-1H-inden-2-yl)carbamate

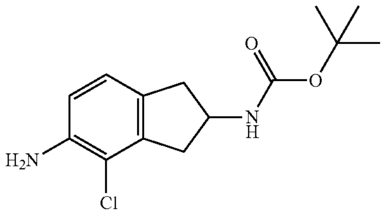 [SMILES: CC(C)(C)OC(=O)NC1Cc2ccc(N)c(Cl)c2C1]

A solution of tert-butyl (5-amino-2,3-dihydro-1H-inden-2-yl)carbamate (200 mg, 773 μmol, CAS: 246873-45-0) and N-chlorosuccinimide (105 mg, 773 μmol) in DMF (2 ml) was stirred at rt for 2 h. The reaction mixture was poured into water and extracted twice with EtOAc. The combined organic layers were washed once with brine and twice with water, dried over sodium sulfate and concentrated in vacuo. The crude material was purified by flash chromatography, followed by SFC separation of the two obtained regiosiomers to provide the title compound as a off-white solid (10 mg, 5% yield). MS (ESI): m/z=227.1 [M-tBu]+

Step 2: tert-butyl (4,5-dichloro-2,3-dihydro-1H-inden-2-yl)carbamate

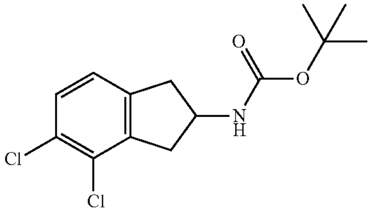 [SMILES: CC(C)(C)OC(=O)NC1Cc2ccc(Cl)c(Cl)c2C1]

To a stirred suspension of $CuCl_2$ (84.1 mg, 620 μmol) in acetonitrile (1 ml) was added tert-butyl nitrite (88.7 mg, 774 μmol) dropwise. The reaction mixture was cooled to 0° C. and a solution of tert-butyl (5-amino-4-chloro-2,3-dihydro-1H-inden-2-yl)carbamate (146 mg, 516 μmol) in acetonitrile (2 ml) was added dropwise over a period of 5 min. The reaction mixture was allowed to warm to rt and stirred for 2 h. The resulting dark mixture was poured into water and extracted twice with EtOAc. The combined organic layers were washed once with brine and twice with water, dried over sodium sulfate and concentrated in vacuo. The crude material was purified by flash chromatography over silica gel using a gradient ethylacetate/heptane 0-50% to provide the title compound as a white solid (102 mg, 65% yield). MS (ESI): m/z=246.1 [M-tBu]+

Step 3: 4,5-dichloro-2,3-dihydro-1H-inden-2-aminium chloride

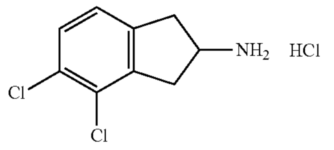 [SMILES: NC1Cc2ccc(Cl)c(Cl)c2C1 ; Cl]

The title compound was prepared from tert-butyl (4,5-dichloro-2,3-dihydro-1H-inden-2-yl)carbamate following procedure described for intermediate A2, step 4 (83% yield, white solid). MS (ESI): m/z=202.1 $[M+H]^+$ Intermediate A4: 6-chloro-4-cyano-2,3-dihydro-1H-inden-2-aminium chloride

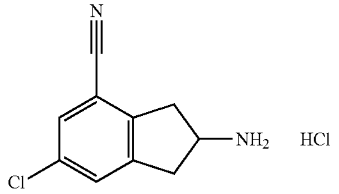 [SMILES: N#Cc1cc(Cl)cc2c1CC(N)C2 ; Cl]

Step 1: tert-butyl (6-chloro-4-cyano-2,3-dihydro-1H-inden-2-yl)carbamate

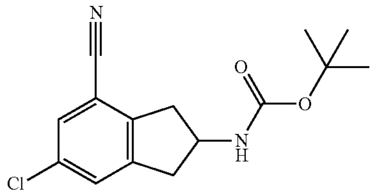 [SMILES: CC(C)(C)OC(=O)NC1Cc2cc(Cl)cc(C#N)c2C1]

2-((tert-butoxycarbonyl)amino)-6-chloro-2,3-dihydro-1H-inden-4-yl trifluoromethanesulfonate (60 mg, 144 µmol, intermediate A2, step 2), zinc cyanide (9.32 mg, 79.4 µmol) and tetrakis(triphenylphosphine) palladium (0) (16.7 mg, 14.4 µmol) were dissolved in dry DMF (721 µl) and Argon was bubbled through the reaction for 5 minutes. Following, the reaction was heated to 110° C. for 2 hours. The reaction was poured into LiCl 10% and extracted with EtOAc. The layers were separated and the aqueous layer was extracted twice more with EtOAc. The combined organic layers were washed with brine, dried over anhydrous sodium sulfate and evaporated to dryness. The crude product was subjected to flash chromatography over silica gel using a gradient ethylacetate/heptane 0-50% to provide the title compound as a white solid (24 mg, 57% yield). MS (ESI): m/z=237.1 $[M\text{-}tBu]^+$ Step 2: 6-chloro-4-cyano-2,3-dihydro-1H-inden-2-aminium chloride

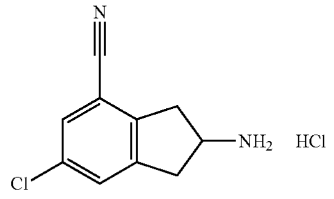 [SMILES: N#Cc1cc(Cl)cc2c1CC(N)C2 ; Cl]

The title compound was prepared from tert-butyl (6-chloro-4-cyano-2,3-dihydro-TH-inden-2-yl)carbamate following procedure described for intermediate A2, step 4 (100% yield, white solid). MS (ESI): m/z=193.1 $[M+H]^+$ Intermediate A5: (S)-6-chloro-4-cyano-2,3-dihydro-TH-inden-2-aminium chloride

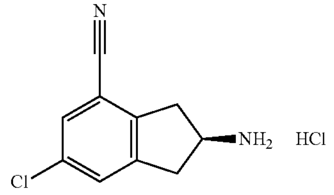 [SMILES: N#Cc1cc(Cl)cc2c1C[C@@H](N)C2 ; Cl]

Step 1: (S)-tert-butyl (6-chloro-4-cyano-2,3-dihydro-TH-inden-2-yl)carbamate

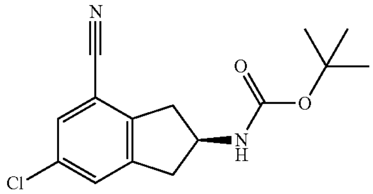 [SMILES: CC(C)(C)OC(=O)N[C@H]1Cc2cc(Cl)cc(C#N)c2C1]

tert-butyl (6-chloro-4-cyano-2,3-dihydro-1H-inden-2-yl) carbamate (65 mg, 222 µmol, Intermediate A4, step 1) was separated on a chiral column (OZ-H, 12 nm, 5 µm, 250×4.6 mm) on SFC condition to provide the title compound as a white solid (32 mg, 49.2% yield, 96% ee, second eluting enantiomere, retention time: 6.6 min.). MS (ESI) m/z: 237.1 $[M\text{-}tBu]^+$ Step 2: (S)-6-chloro-4-cyano-2,3-dihydro-1H-inden-2-aminium chloride

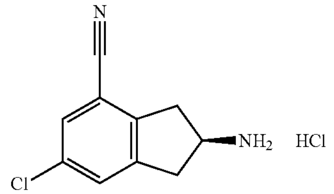 [SMILES: N#Cc1cc(Cl)cc2c1C[C@@H](N)C2 ; Cl]

The title compound was prepared from (S)-tert-butyl (6-chloro-4-cyano-2,3-dihydro-1H-inden-2-yl)carbamate following procedure described for intermediate A2, step 4 (100% yield, white solid). MS (ESI): m/z=193.1 $[M+H]^+$ Intermediate A6: 6-chloro-4-(difluoromethoxy)-2,3-dihydro-1H-inden-2-aminium chloride

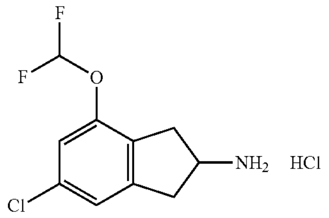 [SMILES: NC1Cc2cc(Cl)cc(OC(F)F)c2C1 ; Cl]

Step 1: tert-butyl (6-chloro-4-(difluoromethoxy)-2,3-dihydro-1H-inden-2-yl)carbamate

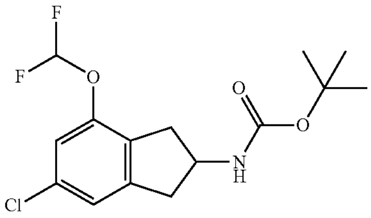 [SMILES: CC(C)(C)OC(=O)NC1Cc2cc(Cl)cc(OC(F)F)c2C1]

Tert-butyl (6-chloro-4-hydroxy-2,3-dihydro-1H-inden-2-yl)carbamate (intermediate A2, step 1) (70 mg, 247 μmol) and potassium hydroxide (138 mg, 2.47 mmol) were dissolved in a mixture of MeCN (1.23 ml) and water (1.23 ml). The mixture was cooled to 0° C. and diethyl (bromodifluoromethyl)phosphonate (132 mg, 87.7 μl, 493 μmol) was added. The reaction was stirred at 0° C. for 1 hour and allowed to warm to rt subsequently. The reaction was stirred at rt for 18 hours. After this time, a second portion of diethyl (bromodifluoromethyl)phosphonate (132 mg, 87.7 μl, 493 μmol) was added. The solvent was evaporated and the was taken up in water and extracted with EtOAc. The layers were separated and the aqueous layer was extracted twice more with EtOAc. The combined organic layers were washed with brine, dried over anhydrous sodium sulfate and evaporated to dryness. The crude product was subjected to flash chromatography over silica gel using a gradient ethylacetate/heptane 0-100% to provide the title compound as a colorless oil (42 mg, 47% yield). MS (ESI): m/z=378.3 $[M+HCOO]^+$ Step 2: 6-chloro-4-(difluoromethoxy)-2,3-dihydro-1H-inden-2-aminium chloride

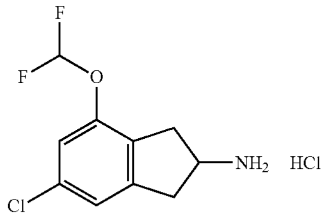 [SMILES: NC1Cc2cc(Cl)cc(OC(F)F)c2C1 ; Cl]

The title compound was prepared from tert-butyl (6-chloro-4-(difluoromethoxy)-2,3-dihydro-1H-inden-2-yl) carbamate following procedure described for intermediate A2, step 4 (96% yield, white solid). MS (ESI): m/z=234.1 $[M+H]^+$ Intermediate A7: 5-chloro-4-methyl-2,3-dihydro-1H-inden-2-aminium chloride

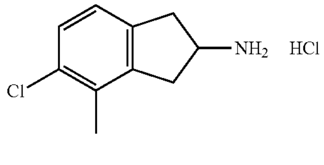

Step 1: tert-butyl (5-amino-6-chloro-2,3-dihydro-1H-inden-2-yl)carbamate

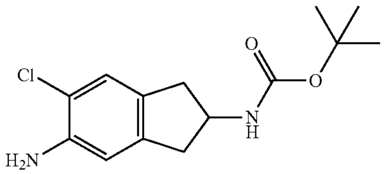

A solution of tert-butyl (5-amino-2,3-dihydro-1H-inden-2-yl)carbamate (200 mg, 773 μmol, CAS: 246873-45-0) and N-chlorosuccinimide (105 mg, 773 μmol) in DMF (2 ml) was stirred at rt for 2 h. The reaction mixture was poured into water and extracted twice with EtOAc. The combined organic layers were washed once with brine and twice with water, dried over sodium sulfate and concentrated in vacuo. The crude material was purified by flash chromatography over silica gel using a gradient ethylacetate/heptane 0-50% to provide the title compound as a yellow gum (48 mg, 16% yield). MS (ESI): m/z=227.1 $[M-tBu]^+$ Step 2: tert-butyl (5-amino-6-chloro-4-iodo-2,3-dihydro-1H-inden-2-Yl)carbamate

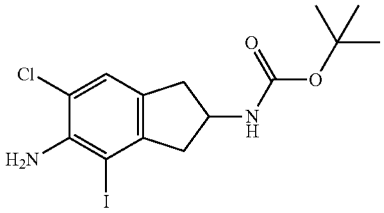 [SMILES: CC(C)(C)OC(=O)NC1Cc2cc(Cl)c(N)c(I)c2C1]

To a stirred solution of tert-butyl (5-amino-6-chloro-2,3-dihydro-1H-inden-2-yl)carbamate (47 mg, 123 μmol) in DMF (2 ml) was added N-iodo-succinimide (29.1 mg, 129 μmol). The resulting dark brown solution was stirred at rt for 20 h, poured into water and extracted twice with EtOAc. The combined organic layers were dried over sodium sulfate and concentrated in vacuo. The crude material was purified by flash chromatography over silica gel using a gradient ethylacetate/heptane 0-50% to provide the title compound as a white solid (37 mg, 74% yield). MS (ESI): m/z=353.0 [M-tBu]+

Step 3: tert-butyl (5-amino-6-chloro-4-methyl-2,3-dihydro-1H-inden-2-yl)carbamate

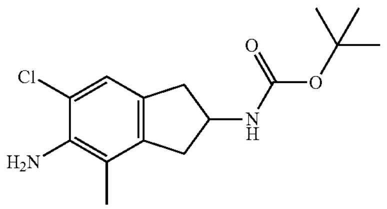 [SMILES: Cc1c(N)c(Cl)cc2c1CC(NC(=O)OC(C)(C)C)C2]

A mixture of tert-butyl (5-amino-6-chloro-4-iodo-2,3-dihydro-1H-inden-2-yl)carbamate (36 mg, 88.1 μmol), trimethylboroxine (15.6 mg, 17.4 μl, 123 μmol), potassium carbonate (18.3 mg, 132 μmol) and tetrakistriphenylposphinepalladium (0) (5.14 mg, 4.4 μmol) in dioxane (750 μl) and water (250 μl) was heated to 110° C. and stirred for 15 h. The reaction mixture was poured into water and extracted twice with EtOAc. The combined organic layers were dried over sodiumsulfate and concentrated in vacuo. The crude material was purified by flash chromatography over silica gel using a gradient ethylacetate/heptane 0-50% to provide the title compound as a colorless gum (21 mg, 80% yield). MS (ESI): m/z=241.1 [M-tBu]+

Step 4: tert-butyl (5-amino-4-methyl-2,3-dihydro-1H-inden-2-yl)carbamate

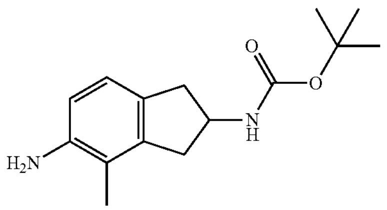 [SMILES: Cc1c(N)ccc2c1CC(NC(=O)OC(C)(C)C)C2]

Tert-butyl (5-amino-6-chloro-4-methyl-2,3-dihydro-1H-inden-2-yl)carbamate (152 mg, 512 μmol) was dissolved in methanol (5 ml), Pd/C (54.5 mg, 51.2 μmol) was added and the reaction mixture was stirred at rt for 15 h. The reaction mixture was filtered through celite and concentrated in vacuo to provide the title compound as light grey solid (130 mg, 97% yield). MS (ESI): m/z=207.2 [M-tBu]+

Step 5: 5-chloro-4-methyl-2,3-dihydro-1H-inden-2-aminium chloride

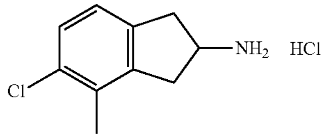

The title compound was prepared from tert-butyl (5-amino-4-methyl-2,3-dihydro-1H-inden-2-yl)carbamate following procedure described for intermediate A2, step 4 (80% yield, off-white solid). MS (ESI): m/z=182.1 [M+H]+

Intermediate A8: 6-chloro-4-(prop-1-yn-1-yl)-2,3-dihydro-1H-inden-2-aminium chloride

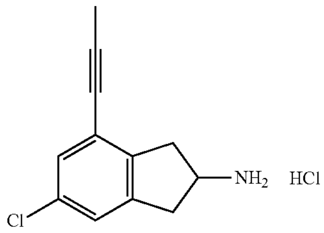

Step 1: tert-butyl (6-chloro-4-cyano-2,3-dihydro-1H-inden-2-yl)carbamate

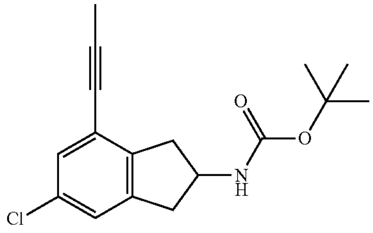 [SMILES: CC#Cc1cc(Cl)cc2c1CC(NC(=O)OC(C)(C)C)C2]

2-((tert-butoxycarbonyl)amino)-6-chloro-2,3-dihydro-1H-inden-4-yl trifluoromethanesulfonate (80 mg, 192 μmol, intermediate A2, step 2), trimethyl(prop-1-yn-1-yl)silane (64.8 mg, 56.7 μl, 577 μmol), triethylamine (58.4 mg, 80.4 μl, 577 μmol), Bis(diphenylphosphino)ferrocene]dichloropalladium(II) (42.2 mg, 57.7 μmol), potassium fluoride (33.5 mg, 577 μmol) and copper (I) iodide (5.5 mg, 28.9 μmol) were suspended in dry DMF (1.28 ml). Argon was bubbled through the solution for 5 minutes. The reaction was then heated to 80° C. for 4 hours. The reaction was diluted with EtOAc and poured into a 10% LiCl solution. The layers were separated and the aqueous layer was extracted twice more with EtOAc. The combined organic layers were washed with brine, dried over anhydrous sodium sulfate, filtered through celite and evaporated to dryness. The crude product was subjected to flash chromatography over silica gel using a gradient ethylacetate/heptane 0-100% to provide the title compound as a yellow oil (57 mg, 97% yield). MS (ESI): m/z=250.1 [M-tBu]+

Step 2: 6-chloro-4-(prop-1-yn-1-yl)-2,3-dihydro-1H-inden-2-aminium chloride

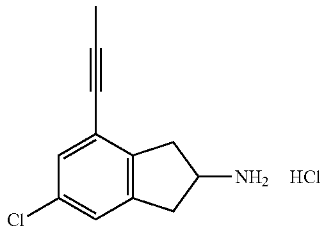

The title compound was prepared from tert-butyl (6-chloro-4-cyano-2,3-dihydro-1H-inden-2-yl)carbamate following procedure described for intermediate A2, step 4 (100% yield, light brown solid). MS (ESI): m/z=206.1 $[M+H]^+$ Intermediate A9: 6-chloro-4-fluoro-2,3-dihydro-1H-inden-2-aminium chloride

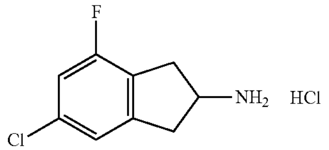 [SMILES: NC1Cc2cc(Cl)cc(F)c2C1 ; Cl]

Step 1: 1,2-bis(bromomethyl)-5-chloro-3-fluoro-benzene

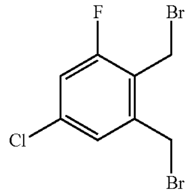 [SMILES: Fc1cc(Cl)cc(CBr)c1CBr]

A suspension of 2-(bromomethyl)-5-chloro-1-fluoro-3-methylbenzene (620 mg, 2.61 mmol, CAS: 1807268-05-8), N-bromsuccinimide (516 mg, 2.87 mmol) and AIBN (8.75 mg, 52.2 μmol) in $CCl_4$ (15 ml) was heated to 85° C. and stirred for 15 h. The reaction mixture was filtered through sintered glass and concentrated in vacuo. The residue was purified by flash chromatography over silica gel using a gradient ethylacetate/heptane 0-20% to provide the title compound as a colorless oil (698 mg, 67% yield).

Step 2: dimethyl 6-chloro-4-fluoro-1,3-dihydro-2H-indene-2,2-dicarboxylate

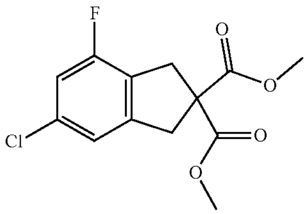 [SMILES: COC(=O)C1(C(=O)OC)Cc2cc(Cl)cc(F)c2C1]

To a solution of dimethyl malonate (131 mg, 114 μl, 973 μmol) in THF (2 ml) was added NaH (38.9 mg, 973 μmol) at 0° C. After stirring at 0° C. for 15 min, a solution of 1,2-bis(bromomethyl)-5-chloro-3-fluorobenzene (350 mg, 885 μmol) in THF (3 ml) was added dropwise at 0° C. After stirring at 0° C. for 15 min, NaH (38.9 mg, 973 μmol) was added again. The reaction mixture was allowed to warm to rt and stirred for 15 h. The resulting suspension was poured into a saturated ammonium chloride solution and extracted twice with EtOAc. The combined organic layers were dried over sodium sulfate and concentrated in vacuo. The crude material was purified by flash chromatography over silica gel using a gradient ethylacetate/heptane 0-50% to provide the title compound as a white solid (62 mg, 25% yield). MS (ESI): m/z=287.1 $[M+H]^+$ Step 3: 6-chloro-4-fluoro-2,3-dihydro-1H-indene-2-carboxylic acid

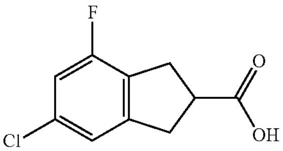 [SMILES: O=C(O)C1Cc2cc(Cl)cc(F)c2C1]

A mixture of dimethyl 6-chloro-4-fluoro-1,3-dihydro-2H-indene-2,2-dicarboxylate (400 mg, 1.4 mmol) and conc. HCl (25%) (6 ml) was heated to 120° C. and stirred for 6 h. 1 ml conc. HCl (25%) was added and the stirring was continued at 120° C. for 1 h. The reaction mixture was extracted twice with EtOAc. The combined organic layers were dried over sodium sulfate and concentrated in vacuo. The crude material was purified by preparative HPLC to provide the title compound as a white solid (137 mg, 46% yield). MS (ESI): m/z=213.1 $[M-H]^+$ Step 4: tert-butyl (6-chloro-4-fluoro-2,3-dihydro-1H-inden-2-yl)carbamate

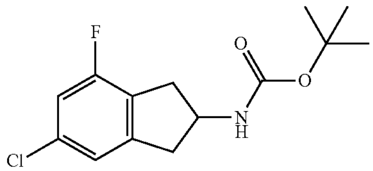 [SMILES: CC(C)(C)OC(=O)NC1Cc2cc(Cl)cc(F)c2C1]

A solution of 6-chloro-4-fluoro-2,3-dihydro-1H-indene-2-carboxylic acid (136 mg, 634 μmol), triethylamine (128 mg, 177 μl, 1.27 mmol) and diphenylphosphoryl azide (187 mg, 146 μl, 665 μmol) in tert-butanol (4 ml) was heated to 50° C. and stirred for 15 h. The reaction mixture was poured into water and extracted twice with EtOAc. The combined organic layers were dried over sodium sulfate and concentrated in vacuo. The crude material was purified by flash chromatography over silica gel using a gradient ethylacetate/heptane 0-50% to provide the title compound as an off-white solid (90 mg, 45% yield). MS (ESI): m/z=230.1 [M-tBu]$^+$ Step 5: 6-chloro-4-fluoro-2,3-dihydro-1H-inden-2-aminium chloride

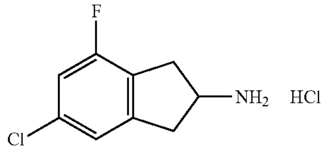 [SMILES: NC1Cc2cc(Cl)cc(F)c2C1 ; Cl]

The title compound was prepared from tert-butyl (6-chloro-4-fluoro-2,3-dihydro-TH-inden-2-yl)carbamate following procedure described for intermediate A2, step 4 (100% yield, off-white solid). MS (ESI): m/z=186.1 [M+H]$^+$ Intermediate A10: 5-chloro-4-fluoro-2,3-dihydro-1H-inden-2-amine

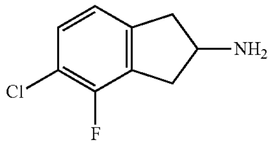 [SMILES: NC1Cc2ccc(Cl)c(F)c2C1]

Step 1: (Z)-5-chloro-4-fluoro-2-(hydroxyimino)-2,3-dihydro-1H-inden-1-one

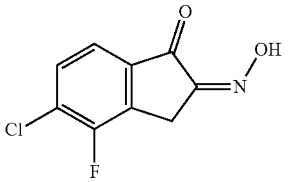 [SMILES: O=C1/C(=N\O)Cc2c1ccc(Cl)c2F]

5-chloro-4-fluoro-2,3-dihydro-TH-inden-1-one (344 mg, 1.86 mmol, CAS: 1260013-11-3) was combined with diethylether (6 ml) to give a white suspension. Then HCl 25% in water (272 mg, 226 μl, 1.86 mmol) was added followed by tert-butyl-nitrite (192 mg, 222 μl, 1.86 mmol) at rt and stirred for 2 hours. The precipitate was filtered and purified by flash chromatography over silica gel using a gradient ethylacetate/heptane 0-60% to provide the title compound as a white solid (250 mg, 63% yield). MS (ESI): m/z=214.1 [M+H]$^+$ Step 2: 5-chloro-4-fluoro-2,3-dihydro-TH-inden-2-amine

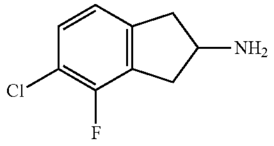 [SMILES: NC1Cc2ccc(Cl)c(F)c2C1]

(Z)-5-chloro-4-fluoro-2-(hydroxyimino)-2,3-dihydro-1H-inden-1-one (100 mg, 0.468 mmol) in acetic acid (2 ml) was hydrogenated under a pressure of 4 bars in the presence of Pd/C 5% (11 mg) and sulfuric acid (100 ul) at room temperature for 16 hours. The catalyst was filtered, washed with methanol, the filtrate was basified to pH 8-9 with a saturated solution of sodium carbonate and diluted with dichloromethane and water. The aqueous layer was extracted twice with dichloromethane. The combined organic layers were dried over sodium sulfate and concentrated in vacuo. The crude material was purified by flash chromatography over silica gel using a gradient dichloromethane/methanol 0-20% to provide the title compound as a colorless oil (50 mg, 42% yield). MS (ESI): m/z=186.1 [M+H]$^+$ Intermediate A11: 6-chloro-4-(trifluoromethyl)-2,3-dihydro-1H-inden-2-aminium chloride

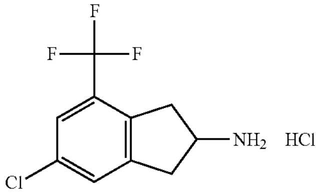 [SMILES: NC1Cc2cc(Cl)cc(C(F)(F)F)c2C1 ; Cl]

Step 1: tert-butyl (6-chloro-4-(trifluoromethyl)-2,3-dihydro-1H-inden-2-yl)carbamate

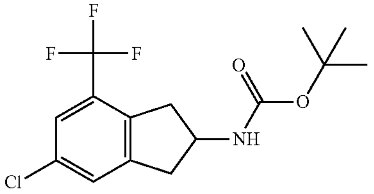 [SMILES: CC(C)(C)OC(=O)NC1Cc2cc(Cl)cc(C(F)(F)F)c2C1]

4-(4,4,5,5-tetramethyl-1,3,2-dioxaborolan-2-yl)-2,3-dihydro-1H-inden-2-yl)carbamate (intermediate A1, step 1) (150 mg, 381 μmol), potassium fluoride (22.1 mg, 381 μmol) and (1,10-Phenanthroline)(trifluoromethyl)copper(I) (trifluoromethylator) (143 mg, 457 μmol) were dissolved in dry DMF (3.81 ml) and air was bubbled through the solution. The reaction was then heated to 50° C. for 4 hours. The reaction was diluted with EtOAc and poured into a 10% LiCl solution. The layers were separated and the aqueous layer was extracted twice more with EtOAc. The combined organic layers were washed with brine, dried over anhydrous sodium sulfate, filtered through celite and evaporated to dryness. The crude product was subjected to flash chromatography over silica gel using a gradient ethylacetate/heptane 0-100% to provide the title compound as an orange solid (24 mg, 13% yield). MS (ESI): m/z=280.1 [M-tBu]$^+$ Step 2: 6-chloro-4-(trifluoromethyl)-2,3-dihydro-1H-inden-2-aminium chloride

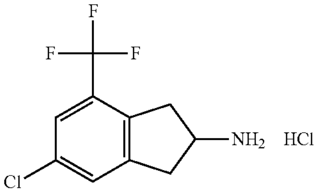 [SMILES: NC1Cc2cc(Cl)cc(C(F)(F)F)c2C1 ; Cl]

The title compound was prepared from tert-butyl (6-chloro-4-(trifluoromethyl)-2,3-dihydro-1H-inden-2-yl) carbamate following procedure described for intermediate A2, step 4 (100% yield, off-white solid). MS (ESI): m/z=236.1 [M+H]$^+$ Intermediates B1-3

Intermediates B1-2 are commercially available or are known and are listed in the following table:

| Int. | Structure | Systematic name | CAS number |
|---|---|---|---|
| B1 | 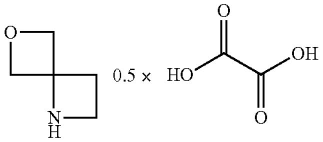 [SMILES: C1CC2(COC2)N1 ; O=C(O)C(=O)O] | 6-oxa-1-aza-spiro[3.3]heptane hemioxalate | 1046153-00-7 |
| B2 | 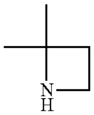 | 2,2-dimethylazetidine | 1086266-55-8 |
| B3 | 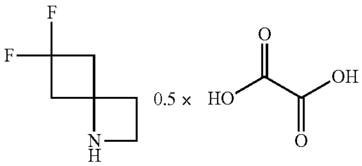 | 6,6-difluoro-1-azaspiro[[3.3]]heptane hemioxalate | 1408074-66-7 |

Intermediate B4: cis-6-methyl-1-azaspiro[3.3]heptan-6-ol bis(2,2,2-trifluoroacetate)

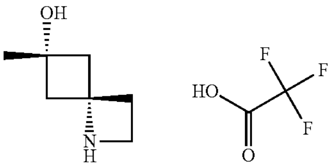

Step 1: cis-tert-butyl-6-hydroxy-6-methyl-1-azaspiro[3.3]heptane-1-carboxylate

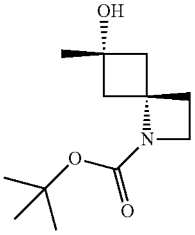 [SMILES: CC(C)(C)OC(=O)N1CC[C@]12C[C@](C)(O)C2]

To a suspension of tert-butyl 6-oxo-1-azaspiro[3.3]heptane-1-carboxylate (500 mg, 2.37 mmol, CAS: 1363380-93-1) in diethyl ether (500 µl) under nitrogen at 0° C., was added methylmagnesium bromide (3M in diethyl ether) (2.37 ml, 7.1 mmol). The reaction mixture was stirred at room temperature for 1.5 hour. The mixture was cooled to 0° C. and carefully quenched with a saturated solution of ammonium chloride. Ethyl acetate was added. Both layers were separated and the aqueous one was extracted twice with ethyl acetate. The combined organic layers were dried over sodium sulfate and evaporated. The crude yellow oil was purified with flash column chromatography over silica gel using a gradient ethylacetate/heptane 0-80% to provide the title compound as a colorless oil (320 mg, 60% yield). MS (ESI): m/z=172.2 [M-tBu]$^+$ Step 2: cis-6-methyl-1-azaspiro[3.3]heptan-6-ol bis (2,2,2-trifluoroacetate)

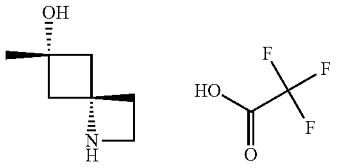

To a mixture of cis-tert-butyl-6-hydroxy-6-methyl-1-azaspiro[3.3]heptane-1-carboxylate (319 mg, 1.4 mmol) in dichloromethane (640 μl) at 0° C. under nitrogen, was added trifluoroacetic acid (1.63 g, 1.1 ml, 14 mmol). The mixture was stirred at room temperature for 2.5 hours. The reaction mixture was evaporated to dryness to provide the title compound (552 mg, 100% yield) as a light yellow oil. MS (ESI): m/z=128.2 $[M+H]^+$ Intermediates C1-3

Intermediate C1: 2-[(4-chloroindan-2-yl)amino] pyrimidine-5-carboxylic acid

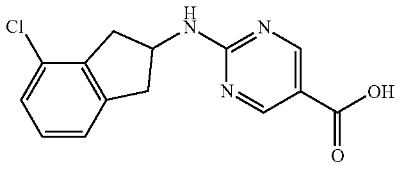 [SMILES: O=C(O)c1cnc(NC2Cc3cccc(Cl)c3C2)nc1]

Step 1: methyl 2-[(4-chloroindan-2-yl)amino]pyrimidine-5-carboxylate

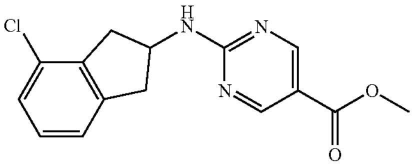 [SMILES: COC(=O)c1cnc(NC2Cc3cccc(Cl)c3C2)nc1]

To a mixture of methyl 2-aminopyrimidine-5-carboxylate (250 mg, 1.63 mmol, CAS: 308348-93-8, commercial) and 4-chloro-1,3-dihydro-2H-inden-2-one (544 mg, 3.26 mmol, CAS: 74124-90-6) in MeCN (2.5 mL) were added TFA (667 μL, 8.65 mmol) and triethylsilane (1.36 mL, 8.49 mmol). The reaction mixture was stirred in a sealed tube at 70° C. overnight then cautiously poured onto a saturated sodium bicarbonate solution and extracted with ethylacatate. The organic layers were washed with brine, dried over sodium sulfate and concentrated. Crude material was purified by flash chromatography over silica gel using a gradient ehylacetate/heptane 0-60% to provide the title compound as a light brown solid (166 mg, 16% yield). MS (ESI): m/z=304.1 $[M+H]^+$ Step 2: 2-[(4-chloroindan-2-yl)amino]pyrimidine-5-carboxylic acid

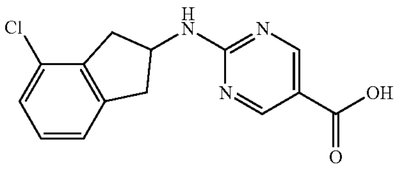 [SMILES: O=C(O)c1cnc(NC2Cc3cccc(Cl)c3C2)nc1]

To a mixture of methyl 2-((4-chloro-2,3-dihydro-1H-inden-2-yl)amino)pyrimidine-5-carboxylate (157 mg, 0.517 mmol) in MeOH (2.5 mL) was added 6M NaOH (103 μL, 0.620 mmol). The suspension was stirred at rt overnight, 6M NaOH (103 μL, 0.620 mmol) was added and the mixture was heated to 50° C. for 9 h. The reaction mixture was cooled to rt and acidified with Amberlite IR-120 and filtered, washed well with DCM/MeOH. The filtrate was evaporated to dryness. The Resin was taken up in 1 M HCl, MeOH was added and the mixture was stirred for 30 min, then filtered. The filtrate was evaporated to dryness to provide the title compound (21 mg, 13% yield) which was used in the next step without purification Intermediate C2: (2-chloropyrimidin-5-yl)(6-oxa-1-azaspiro[3.3]heptan-1-yl)methanone

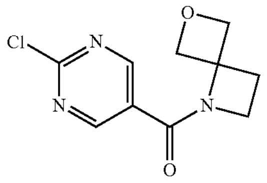 [SMILES: O=C(c1cnc(Cl)nc1)N1CCC12COC2]

To a stirred suspension of 2-chloropyrimidine-5-carboxylic acid (600 mg, 3.78 mmol), N,N-diisoprolethylamine (3.96 ml, 22.7 mmol) and 6-oxa-1-azaspiro[3.3]heptane hemi-oxalate (intermediate B1, 859 mg, 4.54 mmol) in $CH_2Cl_2$ (20 ml) was added 1-propanephosphonic anhydride >50 wt. % in EtOAc (4.51 ml, 7.57 mmol). The reaction mixture was stirred at rt for 2 days, poured into water and extracted twice with $CH_2Cl_2$. The combined organic layers were dried over sodium sulfate and concentrated in vacuo. The crude material was purified by flash chromatography over silica gel using a gradient ehylacetate/heptane 0-100% to provide the title compound as a white solid (250 mg, 28% yield). MS (ESI): m/z=240.1 $[M+H]^+$ Intermediate C3: (S)-2-((6-chloro-4-cyano-2,3-dihydro-1H-inden-2-yl)amino)pyrimidine-5-carboxylic acid

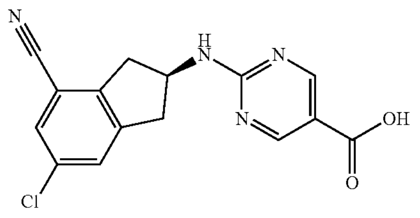 [SMILES: N#Cc1cc(Cl)cc2c1C[C@@H](Nc1ncc(C(=O)O)cn1)C2]

Step 1: Ethyl (S)-2-((6-chloro-4-cyano-2,3-dihydro-1H-inden-2 yl)amino) pyrimidine-5-carboxylate

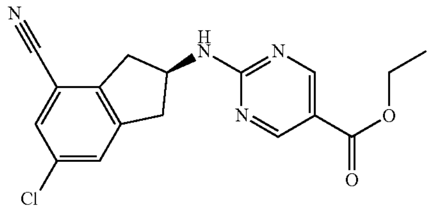 [SMILES: CCOC(=O)c1cnc(N[C@H]2Cc3cc(Cl)cc(C#N)c3C2)nc1]

A suspension of ethyl 2-chloropyrimidine-5-carboxylate (74.8 mg, 393 μmol), (S)-6-chloro-4-cyano-2,3-dihydro-1H-inden-2-aminium chloride (intermediate A5) (75 mg, 327 μmol) and N,N-diisopropylethylamine (130 mg, 171 μl, 982 μmol) in DMA (1.5 ml) was stirred at rt for 15 h. The resulting solution was poured into water and extracted twice with EtOAc. The combined organic layers were dried over sodium sulfate and concentrated in vacuo. The crude material was purified by flash chromatography over silica gel using a gradient ehylacetate/heptane 0-100% to provide the title compound as a white solid (94 mg, 84% % yield). MS (ESI): m/z=343.2 $[M+H]^+$ Step 2: (S)-2-((6-chloro-4-cyano-2,3-dihydro-1H-inden-2-yl)amino)pyrimidine-5-carboxylic acid

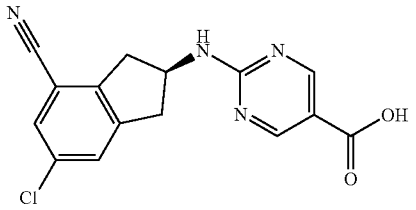 [SMILES: N#Cc1cc(Cl)cc2c1C[C@@H](Nc1ncc(C(=O)O)cn1)C2]

To a solution of ethyl (S)-2-((6-chloro-4-cyano-2,3-dihydro-1H-inden-2-yl)amino)pyrimidine-5-carboxylate (121 mg, 353 μmol) in THF (1.5 ml)/water (0.5 ml) was added lithium hydroxyde monohydrate (37.4 mg, 882 μmol). The reaction mixture was stirred at rt for 15 h, poured into water and extracted twice with EtOAc. The aqueous layer was acidified with 1 N citric acid and extracted twice with EtOAc. The combined organic layers were dried over sodium sulfate and concentrated in vacuo. The residue was triturated with ethylether, filtered through sintered glass and dried in vacuo to provide the title compound (99 mg, 89.1% yield) as a white solid. MS (ESI) m/z: 315.1 $[M+H]^+$

EXAMPLES

Example 1: (2-((4-chloro-2,3-dihydro-1H-inden-2-yl)amino)pyrimidin-5-yl)(6-oxa-1-azaspiro[3.3]heptan-1-yl)methanone

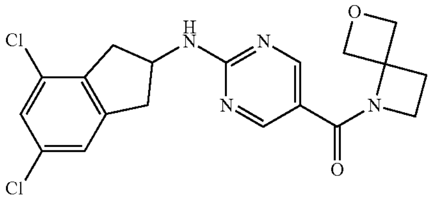 [SMILES: O=C(c1cnc(NC2Cc3cc(Cl)cc(Cl)c3C2)nc1)N1CCC12COC2]

4,6-dichloro-2,3-dihydro-1H-inden-2-aminium 2,2,2-trifluoroacetate (intermediate A1) (50 mg, 158 μmol) was dissolved in DMA (1.58 ml) and diisopropylethylamine (81.8 mg, 110 μl, 633 μmol) was added, followed by (2-chloropyrimidin-5-yl)(6-oxa-1-azaspiro[3.3]heptan-1-yl) methanone (intermediate C2) (37.9 mg, 158 μmol). The reaction was stirred at rt for 20 hours then poured into LiCl 10% and extracted with 2-Me-THF. The layers were separated and the aqueous layer was extracted twice with 2-Me-THF. The combined organic layers were washed with brine, dried over anhydrous sodium sulfate and evaporated to dryness. The crude product was subjected to flash chromatography over silica gel using a gradient ethylacetate/heptane 0-100% to provide the title compound as a white solid (24 mg, 36% % yield). MS (ESI): m/z=405.2 $[M+H]^+$ The following examples 2-10 were prepared in analogy to example 1 from the indicated building blocks A and (2-chloropyrimidin-5-yl)(6-oxa-1-azaspiro[3.3]heptan-1-yl)methanone (intermediate C2)

| Ex. | Structure | name | Building block A | MS (ESI): m/z |
|---|---|---|---|---|
| 2 | 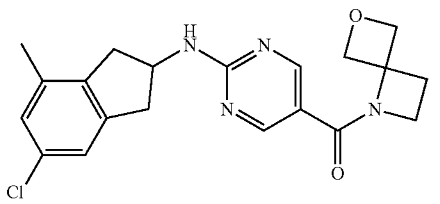 | (2-((6-chloro-4-methyl-2,3-dihydro-1H-inden-2-yl)amino)pyrimidin-5-yl)(6-oxa-1-azaspiro[3.3]heptan-1-yl)methanone | A2 | 385.3 $[M + H]^+$ |
| 3 | 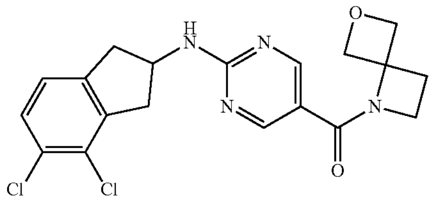 | (2-((4,5-dichloro-2,3-dihydro-1H-inden-2-yl)amino)pyrimidin-5-yl)(6-oxa-1-azaspiro[3.3]heptan-1-yl)methanone | A3 | 405.2 $[M +0 H]^+$ |

-continued

| Ex. | Structure | name | Building block A | MS (ESI): m/z |
|---|---|---|---|---|
| 4 | 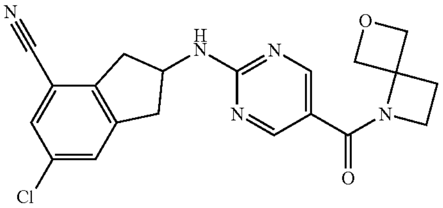 [SMILES: N#Cc1cc(Cl)cc2c1CC(Nc1ncc(C(=O)N3CCC34COC4)cn1)C2] | 2-((5-(6-oxa-1-azaspiro[3.3]heptane-1-carbonyl)pyrimidin-2-yl)amino)-6-chloro-2,3-dihydro-1H-indene-4-carbonitrile | A4 | 396.3 [M + H]$^+$ |
| 5 | 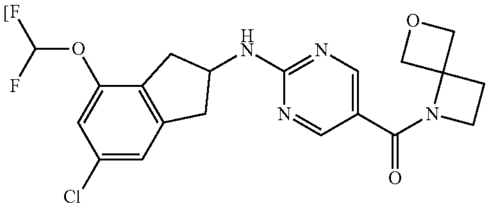 [SMILES: O=C(c1cnc(NC2Cc3cc(Cl)cc(OC(F)F)c3C2)nc1)N1CCC12COC2] | (2-((6-chloro-4-(difluoromethoxy-2,3-dihydro-1H-inden-2-yl)amino)pyrimidin-5-yl)(6-oxa-1-azaspiro[3.3]heplan-1-yl)methanone | A6 | 437.2 [M + H]$^+$ |
| 6 | 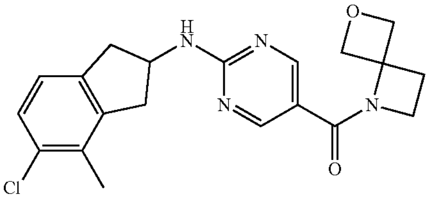 [SMILES: Cc1c(Cl)ccc2c1CC(Nc1ncc(C(=O)N3CCC34COC4)cn1)C2] | (2-((5-chloro-4-methyl-2,3-dihydro-1H-inden-2-yl)arnino)pyrimidin-5-yl)(6-oxa-1-azaspiro[3.3]heplan-1-vhmethanone | A7 | 385.2 [M + H]$^+$ |
| 7 | 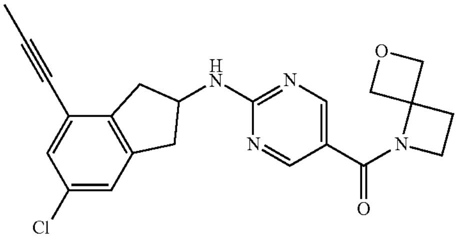 [SMILES: CC#Cc1cc(Cl)cc2c1CC(Nc1ncc(C(=O)N3CCC34COC4)cn1)C2] | (2-((6-chloro-4-(prop-l-yn-1-yl)-2,3-dihydro-lH-inden-2-yl)amino)pyrimidin-5-yl)(6-oxa-1-azaspiro[3.3]heplan-l -yl)methanone | A8 | 409.3 [M + H]$^+$ |
| 8 | 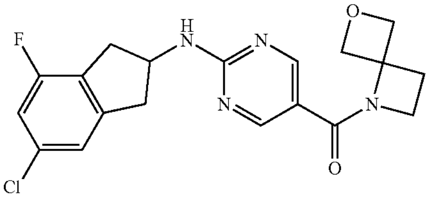 | (2-((6-chloro-4-fluoro-2,3-dihydro-1H-inden-2-yl)amino)pyrimidin-5-yl)(6-oxa-1-azaspiro[3.3]heplan-l -yl)melhanone | A9 | 389.2 [M + H]$^+$ |
| 9 | 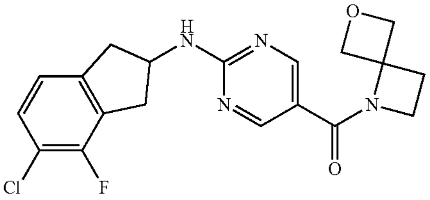 | (2-((5-chloro-4-fluoro-2,3-dihydro-lH-inden-2-yl)amino)pyrimidin-5-yl)(6-oxa-1-azaspiro[3.3]heplan-l -yl)methanone | A10 | 389.3 [M + H]$^+$ |
| 10 | 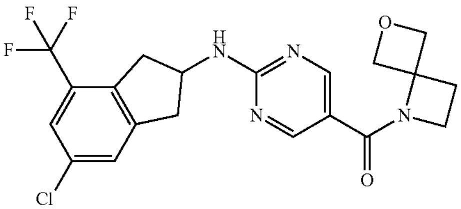 [SMILES: O=C(c1cnc(NC2Cc3cc(Cl)cc(C(F)(F)F)c3C2)nc1)N1CCC12COC2] | (2-((6-chloro-4-(trifluoromethyl)-2,3-dihydro-1 H-inden-2-yl)amino)pyrimidin-5-yl)(6-oxa-1-azaspiro[3.3]heptan-1-yl)melhanone | A11 | 439.3 [M + H]$^+$ |

Example 11: (S)-2-((5-(6-oxa-1-azaspiro[3.3]heptane-1-carbonyl)pyrimidin-2-yl)amino)-6-chloro-2,3-dihydro-1H-indene-4-carbonitrile

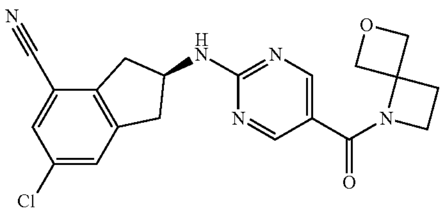 [SMILES: N#Cc1cc(Cl)cc2c1C[C@@H](Nc1ncc(C(=O)N3CCC34COC4)cn1)C2]

To a suspension of (S)-2-((6-chloro-4-cyano-2,3-dihydro-1H-inden-2-yl)amino)pyrimidine-5-carboxylic acid (intermediate C3) (50 mg, 159 μmol) and HATU (72.5 mg, 191 μmol) in DMF (500 μl) was added N,N-diisopropylethylamine (105 mg, 139 μl, 794 μmol). After stirring at rt for 10 min, 6-oxa-1-azaspiro[3.3]heptane hemioxalate (28.3 mg, 95.3 μmol, intermediate B1) was added. The reaction mixture was stirred at rt for 15 h, poured into brine and extracted twice with EtOAc. The combined organic layers were dried over sodium sulfate and concentrated in vacuo. The crude material was purified by flash chromatography over silica gel using a gradient ethylacetate/heptane 0-100% to provide the title compound as a white solid (24 mg, 36% % yield). MS (ESI): m/z=396.2 [M+H]$^+$ The following examples 12-14 were prepared in analogy to example 11 from the indicated building blocks B and (S)-2-((6-chloro-4-cyano-2,3-dihydro-1H-inden-2-yl)amino)pyrimidine-5-carboxylic acid (intermediate C3)

| Ex. | Structure | name | Building block B | MS (ESI): m/z |
|---|---|---|---|---|
| 12 | 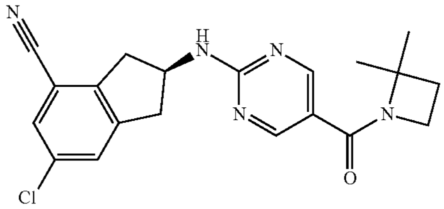 [SMILES: CC1(C)CCN1C(=O)c1cnc(N[C@H]2Cc3cc(Cl)cc(C#N)c3C2)nc1] | (S)-6-chloro-2-((5-(2,2-dimethylazetidine-1-carbonyl)pyrimidin-2-yl)amino)-2.3-dihydro-1H-indene-4-carbonitrile | B2 | 382.2 [M + H]$^+$ |
| 13 | 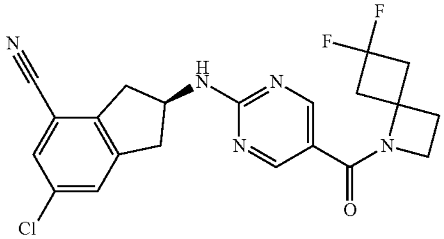 [SMILES: N#Cc1cc(Cl)cc2c1C[C@@H](Nc1ncc(C(=O)N3CCC34CC(F)(F)C4)cn1)C2] | (S)-6-chloro-2-((5-(6,6-difluoro-1-azaspiro[3.3]heptane-1-carbonyl)pyrimidin-2-yl)amino)-2,3-dihydro-1H-indene-4-carbonitrile | B3 | 430.3 [M + H]$^+$ |
| 14 | 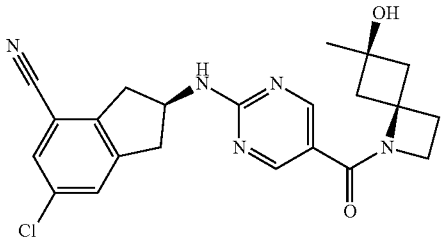 [SMILES: C[C@]1(O)C[C@]2(CCN2C(=O)c2cnc(N[C@H]3Cc4cc(Cl)cc(C#N)c4C3)nc2)C1] | (cis)-6-chloro-2-(S)-((5-(6-hydroxy-6-methyl-1-azaspiro[3.3]heptane-1-carbonyl)pyrirnidin-2-yl)amino)-2,3-dihydro-1H-indene-4-carbonitrile | B4 | 424.3 [M + H]$^+$ |

Example 15: (2-((4-chloro-2,3-dihydro-1H-inden-2-yl)amino)pyrimidin-5-yl)(6-oxa-1-azaspiro[3.3]heptan-1-yl)methanone

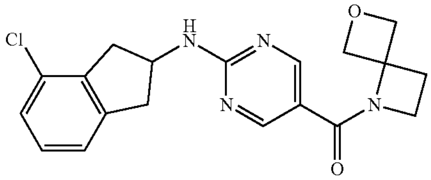 [SMILES: O=C(c1cnc(NC2Cc3cccc(Cl)c3C2)nc1)N1CCC12COC2]

The title compound was prepared in analogy to example 11 from the building block B1 and 2-[(4-chloroindan-2-yl)amino]pyrimidine-5-carboxylic acid (intermediate C1). MS (ESI): m/z=371.2 [M+H]$^+$ Example 16: (S or R)-(2-((6-chloro-4-fluoro-2,3-dihydro-1H-inden-2-yl)amino) pyrimidin-5-yl)(6-oxa-1-azaspiro[3.3]heptan-1-yl)methanone

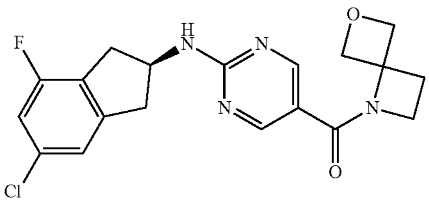 [SMILES: O=C(c1cnc(N[C@H]2Cc3cc(Cl)cc(F)c3C2)nc1)N1CCC12COC2]

The title compound was obtained by chiral HPLC separation of racemic example 8 using SFC method (column: AY-H, 12 nm, 5 μm, 250×4.6 mm) (second eluting enantiomer, retention time: 5.53 min, 98% ee, off-white solid). MS (ESI) m/z: 389.3 $[M+H]^+$ Example A A compound of formula (I) can be used in a manner known per se as the active ingredient for the production of tablets of the following composition:

Per Tablet

| | |
|---|---|
| Active ingredient | 200 mg |
| Microcrystalline cellulose | 155 mg |
| Corn starch | 25 mg |
| Talc | 25 mg |
| Hydroxypropylmethylcellulose | 20 mg |
| | 425 mg |

Example B

A compound of formula (I) can be used in a manner known per se as the active ingredient for the production of capsules of the following composition:

Per Capsule

| | |
|---|---|
| Active ingredient | 100.0 mg |
| Corn starch | 20.0 mg |
| Lactose | 95.0 mg |
| Talc | 4.5 mg |
| Magnesium stearate | 0.5 mg |
| | 220.0 mg |

The invention claimed is:

1. A compound of formula (I)

(I)

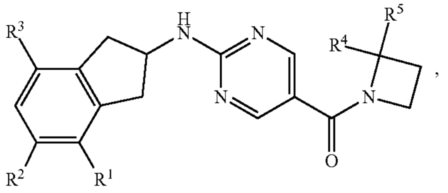

or a pharmaceutically acceptable salt thereof, wherein:

$R^1$, $R^2$, and $R^3$ are independently selected from the group consisting of
- i) H,
- ii) $C_{1-6}$-alkyl,
- iii) $C_{2-6}$-alkynyl,
- iv) halogen,
- v) halo-$C_{1-6}$-alkyl,
- vi) halo-$C_{1-6}$-alkoxy,
- vii) cyano, and
- viii) cyano-$C_{1-6}$-alkyl, wherein at least one of $R^1$ and $R^3$ is other than H;

$R^4$ and $R^5$ are independently selected from the group consisting of
- i) H,
- ii) $C_{1-6}$-alkyl,
- iii) halogen, and
- iv) halo-$C_{1-6}$-alkyl, or $R^4$ and $R^5$ together with the carbon atom to which they are attached form a heterocycloalkyl or a substituted $C_{3-8}$-cycloalkyl, wherein the substituted $C_{3-8}$-cycloalkyl is substituted with $R^6$ and $R^7$; and $R^6$ and $R^7$ are independently selected from the group consisting of halogen, hydroxy, and $C_{1-6}$-alkyl.

2. The compound of claim 1, or a pharmaceutically acceptable salt thereof, wherein $R^1$, $R^2$, and $R^3$ are independently selected from the group consisting of
- i) H,
- ii) $C_{1-6}$-alkyl,
- iii) $C_{2-6}$-alkynyl,
- iv) halogen,
- v) halo-$C_{1-6}$-alkyl
- vi) halo-$C_{1-6}$-alkoxy, and
- vii) cyano;

wherein at least one of $R^1$ and $R^3$ is other than H.

3. The compound of claim 1, or a pharmaceutically acceptable salt thereof, wherein $R^4$ and $R^5$ are independently selected from the group consisting of
- i) H and
- ii) $C_{1-6}$-alkyl, or $R^4$ and $R^5$ together with the carbon atom to which they are attached form a 4-member heterocycloalkyl with a single oxygen or a substituted $C_4$-cycloalkyl, wherein the substituted $C_4$-cycloalkyl is substituted with $R^6$ and $R^7$.

4. The compound of claim 1, or a pharmaceutically acceptable salt thereof, wherein $R^4$ and $R^5$ are independently selected from the group consisting of
- i) H and
- ii) methyl, or $R^4$ and $R^5$ together with the carbon atom to which they are attached form an oxetane ring or a substituted $C_4$-cycloalkyl, wherein the substituted $C_4$-cycloalkyl is substituted with $R^6$ and $R^7$.

5. The compound of claim 1, or a pharmaceutically acceptable salt thereof, wherein $R^6$ and $R^7$ are both halogen; or $R^6$ is hydroxy and $R^7$ is $C_{1-6}$-alkyl.

6. The compound of claim 1, or a pharmaceutically acceptable salt thereof, wherein $R^6$ and $R^7$ are both fluorine; or $R^6$ is hydroxy and $R^7$ is methyl.

7. The compound of claim 1, or a pharmaceutically acceptable salt thereof, wherein $R^1$, $R^2$, and $R^3$ are independently selected from the group consisting of i) H,
ii) $C_{1-6}$-alkyl,
iii) $C_{2-6}$-alkynyl,
iv) halogen,
v) halo-$C_{1-6}$-alkyl,
vi) halo-$C_{1-6}$-alkoxy, and
vii) cyano;

wherein at least one of $R^1$ and $R^3$ is other than H;

$R^4$ and $R^5$ are independently selected from the group consisting of i) H and
ii) methyl, or $R^4$ and $R^5$ together with the carbon atom to which they are attached form an oxetane ring or a substituted $C_4$-cycloalkyl, wherein the substituted $C_4$-cycloalkyl is substituted with $R^6$ and $R^7$; and $R^6$ and $R^7$ are both fluorine; or $R^6$ is hydroxy and $R^7$ is methyl.

8. The compound of claim 1, selected from the group consisting of (2-((4-chloro-2,3-dihydro-1H-inden-2-yl) amino) pyrimidin-5-yl)(6-oxa-1-azaspiro[3.3]heptan-1-yl) methanone;

(2-((4,6-dichloro-2,3-dihydro-1H-inden-2-yl) amino) pyrimidin-5-yl)(6-oxa-1-azaspiro[3.3]heptan-1-yl) methanone;

(2-((6-chloro-4-methyl-2,3-dihydro-1H-inden-2-yl) amino) pyrimidin-5-yl)(6-oxa-1-azaspiro[3.3]heptan-1-yl) methanone;

(2-((4,5-dichloro-2,3-dihydro-1H-inden-2-yl) amino) pyrimidin-5-yl)(6-oxa-1-azaspiro[3.3]heptan-1-yl) methanone;

2-((5-(6-oxa-1-azaspiro[3.3]heptane-1-carbonyl) pyrimidin-2-yl) amino)-6-chloro-2,3-dihydro-1H-indene-4-carbonitrile;

(S)-2-((5-(6-oxa-1-azaspiro[3.3]heptane-1-carbonyl) pyrimidin-2-yl) amino)-6-chloro-2,3-dihydro-1H-indene-4-carbonitrile;

(2-((6-chloro-4-(difluoromethoxy)-2,3-dihydro-1H-inden-2-yl) amino) pyrimidin-5-yl)(6-oxa-1-azaspiro[3.3]heptan-1-yl) methanone;

(2-((5-chloro-4-methyl-2,3-dihydro-1H-inden-2-yl) amino) pyrimidin-5-yl)(6-oxa-1-azaspiro[3.3]heptan-1-yl) methanone;

(2-((6-chloro-4-(prop-1-yn-1-yl)-2,3-dihydro-1H-inden-2-yl) amino) pyrimidin-5-yl)(6-oxa-1-azaspiro[3.3]heptan-1-yl) methanone;

(2-((6-chloro-4-fluoro-2,3-dihydro-1H-inden-2-yl) amino) pyrimidin-5-yl)(6-oxa-1-azaspiro[3.3]heptan-1-yl) methanone;

(2-((5-chloro-4-fluoro-2,3-dihydro-1H-inden-2-yl) amino) pyrimidin-5-yl)(6-oxa-1-azaspiro[3.3]heptan-1-yl) methanone;

(S or R)-(2-((6-chloro-4-fluoro-2,3-dihydro-1H-inden-2-yl) amino) pyrimidin-5-yl)(6-oxa-1-azaspiro[3.3]heptan-1-yl) methanone;

(2-((6-chloro-4-(trifluoromethyl)-2,3-dihydro-1H-inden-2-yl) amino) pyrimidin-5-yl)(6-oxa-1-azaspiro[3.3]heptan-1-yl) methanone;

(S)-6-chloro-2-((5-(6,6-difluoro-1-azaspiro[3.3]heptane-1-carbonyl) pyrimidin-2-yl) amino)-2,3-dihydro-1H-indene-4-carbonitrile;

(S)-6-chloro-2-((5-(2,2-dimethylazetidine-1-carbonyl) pyrimidin-2-yl) amino)-2,3-dihydro-1H-indene-4-carbonitrile; and (cis)-6-chloro-2-(S)-((5-(6-hydroxy-6-methyl-1-azaspiro[3.3]heptane-1-carbonyl) pyrimidin-2-yl) amino)-2,3-dihydro-1H-indene-4-carbonitrile;

or a pharmaceutically acceptable salt thereof.

9. A process to prepare a compound of claim 1, or a pharmaceutically acceptable salt thereof, the process comprising the reaction of a compound of formula (II) in the presence of a compound of formula (III) to provide a compound of formula (I), wherein $R^1$, $R^2$, $R^3$, $R^4$, and $R^5$ are as defined in claim 1:

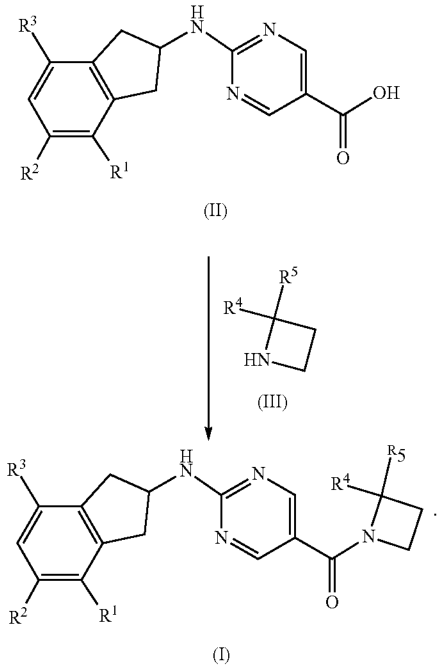

10. A pharmaceutical composition comprising a compound of claim 1, or a pharmaceutically acceptable salt thereof, and a therapeutically inert carrier.

11. A pharmaceutical composition comprising a compound of claim 8, or a pharmaceutically acceptable salt thereof, and a therapeutically inert carrier.

* * * * *